(12) United States Patent  
Stewart et al.

(10) Patent No.: US 7,706,894 B2  
(45) Date of Patent: Apr. 27, 2010

(54) HEART WALL ABLATION/MAPPING CATHETER AND METHOD

(75) Inventors: Mark T. Stewart, Lino Lakes, MN (US); Johnson E. Goode, Maple Grove, MN (US); James M. Speckien, Vadnais Heights, MN (US); Mark A. Taube, Andover, MN (US); Eduardo N. Warman, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1259 days.

(21) Appl. No.: 11/115,028

(22) Filed: Apr. 26, 2005

(65) Prior Publication Data

US 2005/0273006 A1 Dec. 8, 2005

(51) Int. Cl.
*A61N 1/05* (2006.01)

(52) U.S. Cl. ..................................... 607/122

(58) Field of Classification Search ... 604/95.01–95.05, 604/99.04; 607/122; 606/41; 600/433, 466, 600/146–150
See application file for complete search history.

(56) References Cited

U.S. PATENT DOCUMENTS 3,736,936 A 6/1973 Basiulis et al.

(Continued)

FOREIGN PATENT DOCUMENTS

WO WO 93/20877 10/1993

(Continued)

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner*—Mark W Bockelman
*Assistant Examiner*—Roland Dinga

(57) ABSTRACT

Steerable electrophysiology catheters for use in mapping and/or ablation of accessory pathways in myocardial tissue of the heart wall and methods of use thereof are disclosed. The catheter comprises a catheter body and handle, the catheter body having a proximal section and a distal section and manipulators that enable the deflection of a distal segment of the distal tip section with respect to the independently formed curvature of a proximal segment of the distal tip section through a bending or knuckle motion of an intermediate segment between the proximal and distal segments. A wide angular range of deflection within a very small curve or bend radius in the intermediate segment is obtained. At least one distal tip electrode is preferably confined to the distal segment which can have a straight axis extending distally from the intermediate segment. The curvature of the proximal segment and the bending angle of the intermediate segment are independently selectable. The axial alignment of the distal segment with respect to the nominal axis of the proximal shaft section of the catheter body can be varied between substantially axially aligned (0° curvature) in an abrupt knuckle bend through a range of about −90° to about +180° within a bending radius of between about 2.0 mm and 7.0 mm and preferably less than 5.0 mm. The proximal segment curve can be independently formed in a range of about −180° through about +270° with respect to the axis of the proximal shaft section to provide an optimum angular orientation of the distal electrode(s). The distal segment can comprise a highly flexible elongated distal segment body and electrode(s) that conform with the shape and curvature of the heart wall.

2 Claims, 16 Drawing Sheets

U.S. PATENT DOCUMENTS

| | | |
|---|---|---|
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,377,168 A | 3/1983 | Rzasa et al. |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,909,787 A | 3/1990 | Danforth |
| 4,916,922 A | 4/1990 | Mullens |
| 4,917,095 A | 4/1990 | Fry et al. |
| 4,936,281 A | 6/1990 | Stasz |
| 4,946,460 A | 8/1990 | Merry et al. |
| 5,013,312 A | 5/1991 | Parins et al. |
| 5,029,574 A | 7/1991 | Shimamura et al. |
| 5,044,165 A | 9/1991 | Linner et al. |
| 5,058,595 A | 10/1991 | Kern |
| 5,078,713 A | 1/1992 | Varney |
| 5,080,102 A | 1/1992 | Dory |
| 5,080,660 A | 1/1992 | Buelina |
| 5,100,388 A | 3/1992 | Behl et al. |
| 5,108,390 A | 4/1992 | Potocky et al. |
| 5,147,355 A | 9/1992 | Freidman et al. |
| 5,178,133 A | 1/1993 | Pena |
| 5,195,968 A | 3/1993 | Lundquist et al. |
| 5,203,776 A | 4/1993 | Durfee |
| 5,207,674 A | 5/1993 | Hamilton |
| 5,215,540 A | 6/1993 | Anderhub |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,238,005 A | 8/1993 | Imran |
| 5,254,088 A | 10/1993 | Lundquist et al. |
| 5,254,116 A | 10/1993 | Baust et al. |
| 5,263,493 A | 11/1993 | Avitall |
| 5,269,291 A | 12/1993 | Carter |
| 5,273,535 A | 12/1993 | Edwards et al. |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,299,574 A | 4/1994 | Bower |
| 5,306,263 A | 4/1994 | Voda |
| 5,309,896 A | 5/1994 | Moll et al. |
| 5,314,451 A | 5/1994 | Mulier |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,327,905 A | 7/1994 | Avitall |
| 5,334,181 A | 8/1994 | Rubinsky et al. |
| 5,334,193 A | 8/1994 | Nardella |
| 5,348,554 A | 9/1994 | Imran et al. |
| 5,353,783 A | 10/1994 | Nakao et al. |
| 5,353,800 A | 10/1994 | Mulier |
| 5,354,258 A | 10/1994 | Dory |
| 5,354,297 A | 10/1994 | Avitall |
| 5,358,479 A | 10/1994 | Wilson |
| 5,361,752 A | 11/1994 | Moll et al. |
| 5,368,564 A | 11/1994 | Savage |
| 5,370,678 A | 12/1994 | Edwards et al. |
| 5,385,148 A | 1/1995 | Lesh et al. |
| 5,396,887 A | 3/1995 | Imran |
| 5,397,304 A | 3/1995 | Truckai |
| 5,397,321 A | 3/1995 | Houser et al. |
| 5,400,770 A | 3/1995 | Nakao et al. |
| 5,400,783 A | 3/1995 | Pomeranz et al. |
| 5,402,794 A | 4/1995 | Mulier |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,441,483 A | 8/1995 | Avitall |
| 5,443,463 A | 8/1995 | Stern et al. |
| 5,443,470 A | 8/1995 | Stern et al. |
| 5,445,148 A | 8/1995 | Jaraczewski et al. |
| 5,450,843 A | 9/1995 | Moll et al. |
| 5,452,582 A | 9/1995 | Longsworth |
| 5,452,733 A | 9/1995 | Sterman et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,507,725 A * | 4/1996 | Savage et al. ............ 604/95.04 |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,545,195 A | 8/1996 | Lennox et al. |
| 5,545,200 A | 8/1996 | West et al. |
| 5,549,581 A | 8/1996 | Lurie et al. |
| 5,549,661 A | 8/1996 | Kordis et al. |
| 5,555,883 A | 9/1996 | Avitall |
| 5,558,671 A | 9/1996 | Yates |
| 5,560,362 A | 10/1996 | Silwa, Jr. et al. |

| | | | | | | |
|---|---|---|---|---|---|---|
| 5,562,720 A | 10/1996 | Stern et al. | | 5,823,955 A * | 10/1998 | Kuck et al. ............... 600/374 |
| 5,569,241 A | 10/1996 | Edwards | | 5,827,216 A | 10/1998 | Igo et al. |
| 5,571,088 A | 11/1996 | Lennox et al. | | 5,827,278 A | 10/1998 | Webster, Jr. |
| 5,571,215 A | 11/1996 | Sterman et al. | | 5,827,296 A | 10/1998 | Morris et al. |
| 5,573,532 A | 11/1996 | Chang et al. | | 5,836,947 A | 11/1998 | Fleischman et al. |
| 5,575,766 A | 11/1996 | Swartz et al. | | 5,840,030 A | 11/1998 | Ferek-Petric et al. |
| 5,575,788 A | 11/1996 | Baker et al. | | 5,844,349 A | 12/1998 | Oakley et al. |
| 5,575,810 A | 11/1996 | Swanson et al. | | 5,846,187 A | 12/1998 | Wells et al. |
| 5,578,007 A | 11/1996 | Imran | | 5,846,191 A | 12/1998 | Wells et al. |
| 5,582,609 A * | 12/1996 | Swanson et al. ............... 606/39 | | 5,849,028 A | 12/1998 | Chen |
| 5,588,432 A | 12/1996 | Crowley | | 5,853,368 A | 12/1998 | Solomon et al. |
| 5,590,657 A | 1/1997 | Cain et al. | | 5,871,523 A | 2/1999 | Fleischman et al. |
| 5,595,183 A | 1/1997 | Swanson et al. | | 5,871,525 A | 2/1999 | Edwards et al. |
| 5,603,697 A | 2/1997 | Grundy et al. | | 5,871,530 A | 2/1999 | Williams et al. |
| 5,607,462 A | 3/1997 | Imran | | 5,873,845 A | 2/1999 | Cline et al. |
| 5,609,151 A | 3/1997 | Mulier | | 5,876,398 A | 3/1999 | Mulier |
| 5,611,777 A | 3/1997 | Bowden et al. | | 5,876,399 A | 3/1999 | Chia et al. |
| 5,617,854 A | 4/1997 | Munsif | | 5,879,295 A | 3/1999 | Li et al. |
| 5,626,136 A | 5/1997 | Webster, Jr. | | 5,879,296 A | 3/1999 | Ockuly et al. |
| 5,630,837 A | 5/1997 | Crowley | | 5,881,727 A | 3/1999 | Edwards |
| 5,637,090 A | 6/1997 | McGee et al. | | 5,881,732 A | 3/1999 | Sung et al. |
| 5,643,197 A | 7/1997 | Brucker et al. | | 5,882,346 A | 3/1999 | Pomeranz et al. |
| 5,656,029 A | 8/1997 | Imran et al. | | 5,885,278 A | 3/1999 | Fleischman |
| 5,658,278 A | 8/1997 | Imran et al. | | 5,893,848 A | 4/1999 | Negus et al. |
| 5,671,747 A | 9/1997 | Connor | | 5,895,417 A | 4/1999 | Pomeranz et al. |
| 5,673,695 A | 10/1997 | McGee et al. | | 5,897,529 A | 4/1999 | Ponzi |
| 5,676,662 A | 10/1997 | Fleischhacker et al. | | 5,897,553 A | 4/1999 | Mulier |
| 5,676,692 A | 10/1997 | Sanghvi et al. | | 5,897,554 A | 4/1999 | Chia et al. |
| 5,676,693 A | 10/1997 | Lafontaine | | 5,899,898 A | 5/1999 | Arless et al. |
| 5,678,550 A | 10/1997 | Bassen et al. | | 5,899,899 A | 5/1999 | Arless et al. |
| 5,680,860 A | 10/1997 | Imran | | 5,902,289 A | 5/1999 | Swartz et al. |
| 5,681,278 A | 10/1997 | Igo et al. | | 5,904,667 A | 5/1999 | Falwell |
| 5,681,308 A | 10/1997 | Edwards et al. | | 5,904,711 A | 5/1999 | Flom et al. |
| 5,685,878 A | 11/1997 | Falwell et al. | | 5,906,580 A | 5/1999 | Kline-Schoder et al. |
| 5,687,723 A | 11/1997 | Avitall | | 5,906,587 A | 5/1999 | Zimmon |
| 5,687,737 A | 11/1997 | Branham et al. | | 5,906,606 A | 5/1999 | Chee et al. |
| 5,688,267 A | 11/1997 | Panescu et al. | | 5,906,613 A | 5/1999 | Mulier |
| 5,690,611 A | 11/1997 | Swartz et al. | | 5,908,029 A | 6/1999 | Knudson et al. |
| 5,697,536 A | 12/1997 | Eggers et al. | | 5,916,213 A * | 6/1999 | Haissaguerre et al. ......... 606/41 |
| 5,697,882 A | 12/1997 | Eggers et al. | | 5,916,214 A * | 6/1999 | Cosio et al. ................... 606/41 |
| 5,697,925 A | 12/1997 | Taylor | | 5,921,924 A | 7/1999 | Avitall |
| 5,697,927 A | 12/1997 | Imran et al. | | 5,921,982 A | 7/1999 | Lesh et al. |
| 5,697,928 A | 12/1997 | Walcott et al. | | 5,927,284 A | 7/1999 | Borst et al. |
| 5,713,942 A | 2/1998 | Stern | | 5,928,191 A | 7/1999 | Houser et al. |
| 5,716,389 A | 2/1998 | Walinsky et al. | | 5,931,810 A | 8/1999 | Grabek |
| 5,718,241 A | 2/1998 | Ben-Haim et al. | | 5,931,848 A | 8/1999 | Saadat |
| 5,718,701 A | 2/1998 | Shai et al. | | 5,935,102 A | 8/1999 | Bowden et al. |
| 5,720,775 A | 2/1998 | Larnard | | 5,935,124 A | 8/1999 | Klumb et al. |
| 5,722,402 A | 3/1998 | Swanson et al. | | 5,938,616 A | 8/1999 | Eaton et al. |
| 5,725,524 A | 3/1998 | Mulier | | 5,938,694 A | 8/1999 | Jaraczewski et al. |
| 5,730,074 A | 3/1998 | Peter | | 5,944,690 A | 8/1999 | Falwell et al. |
| 5,730,127 A | 3/1998 | Avitall | | 5,954,654 A | 9/1999 | Eaton et al. |
| 5,730,704 A | 3/1998 | Avitall | | 5,954,661 A | 9/1999 | Greenspon et al. |
| 5,733,280 A | 3/1998 | Avitall | | 5,971,980 A | 10/1999 | Sherman |
| 5,735,280 A | 4/1998 | Sherman et al. | | 5,971,983 A | 10/1999 | Lesh |
| 5,735,290 A | 4/1998 | Sherman et al. | | 5,980,516 A | 11/1999 | Mulier |
| 5,755,760 A * | 5/1998 | Maguire et al. ............... 607/122 | | 5,993,447 A | 11/1999 | Blewett et al. |
| 5,769,846 A | 6/1998 | Edwards et al. | | 6,002,955 A | 12/1999 | Willems et al. |
| 5,779,669 A * | 7/1998 | Haissaguerre et al. .... 604/95.01 | | 6,004,269 A | 12/1999 | Crowley et al. |
| 5,782,828 A | 7/1998 | Chen et al. | | 6,007,499 A | 12/1999 | Martin et al. |
| 5,782,890 A | 7/1998 | Wahlstrand et al. | | 6,012,457 A | 1/2000 | Lesh |
| 5,782,899 A | 7/1998 | Imran | | 6,016,809 A | 1/2000 | Mulier |
| 5,785,706 A | 7/1998 | Bednarek | | 6,016,811 A | 1/2000 | Knopp et al. |
| 5,788,636 A | 8/1998 | Curley | | 6,027,473 A | 2/2000 | Ponzi |
| 5,792,140 A | 8/1998 | Tu et al. | | 6,032,061 A | 2/2000 | Koblish |
| 5,797,842 A * | 8/1998 | Pumares et al. ............... 600/435 | | 6,032,674 A | 3/2000 | Eggers et al. |
| 5,797,905 A * | 8/1998 | Fleischman et al. ........... 606/41 | | 6,035,224 A * | 3/2000 | West ........................ 600/373 |
| 5,797,960 A | 8/1998 | Stevens et al. | | 6,038,472 A | 3/2000 | Mulier |
| 5,800,428 A | 9/1998 | Nelson et al. | | 6,042,556 A | 3/2000 | Beach et al. |
| 5,800,482 A | 9/1998 | Pomeranz et al. | | 6,047,700 A | 4/2000 | Eggers et al. |
| 5,807,249 A * | 9/1998 | Qin et al. ................... 600/374 | | 6,063,077 A | 5/2000 | Schaer |
| 5,807,395 A | 9/1998 | Mulier | | 6,063,081 A | 5/2000 | Mulier |
| 5,810,802 A | 9/1998 | Panescu et al. | | 6,066,125 A | 5/2000 | Webster, Jr. |

| Patent | Date | Name |
|---|---|---|
| 6,068,629 A | 5/2000 | Haissaguerre et al. |
| 6,071,279 A | 6/2000 | Whayne et al. |
| 6,088,894 A | 7/2000 | Oakley |
| 6,096,037 A | 8/2000 | Mulier |
| 6,113,592 A | 9/2000 | Taylor |
| 6,117,101 A | 9/2000 | Diederich et al. |
| 6,120,496 A | 9/2000 | Whayne et al. |
| 6,142,993 A | 11/2000 | Whayne et al. |
| 6,142,994 A | 11/2000 | Swanson et al. |
| 6,152,920 A | 11/2000 | Thompson et al. |
| 6,161,543 A | 12/2000 | Cox et al. |
| 6,165,174 A | 12/2000 | Jacobs et al. |
| 6,178,355 B1 | 1/2001 | Williams et al. |
| 6,200,315 B1 * | 3/2001 | Gaiser et al. ............... 606/41 |
| 6,217,528 B1 | 4/2001 | Koblish et al. |
| 6,217,576 B1 | 4/2001 | Tu et al. |
| 6,224,592 B1 | 5/2001 | Eggers et al. |
| 6,228,032 B1 | 5/2001 | Eaton et al. |
| 6,231,518 B1 | 5/2001 | Grabek et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,270,471 B1 | 8/2001 | Hechel et al. |
| 6,293,943 B1 | 9/2001 | Panescu et al. |
| 6,296,619 B1 | 10/2001 | Brisken et al. |
| 6,302,880 B1 | 10/2001 | Schaer |
| 6,302,903 B1 | 10/2001 | Mulier |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,315,778 B1 | 11/2001 | Gambale et al. |
| 6,319,250 B1 | 11/2001 | Falwell et al. |
| 6,325,797 B1 | 12/2001 | Stewart et al. |
| 6,327,505 B1 | 12/2001 | Medhkour et al. |
| 6,328,736 B1 | 12/2001 | Mulier |
| 6,332,881 B1 | 12/2001 | Carner et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,956 B1 | 10/2002 | Hsuan et al. |
| 6,464,698 B1 | 10/2002 | Falwell |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,484,727 B1 | 11/2002 | Vaska et al. |
| 6,488,680 B1 | 12/2002 | Francischelli |
| 6,493,589 B1 | 12/2002 | Mulier |
| 6,494,902 B2 | 12/2002 | Mulier |
| 6,502,575 B1 | 1/2003 | Jacobs et al. |
| 6,514,250 B1 | 2/2003 | Jahns |
| 6,527,767 B2 | 3/2003 | Wang et al. |
| 6,537,248 B2 | 3/2003 | Mulier |
| 6,537,272 B2 | 3/2003 | Christopherson et al. |
| 6,539,265 B2 | 3/2003 | Mulier |
| 6,605,084 B2 | 4/2003 | Acker et al. |
| 6,558,382 B2 | 5/2003 | Jahns |
| 5,697,536 C1 | 6/2003 | Eggers et al. |
| 6,584,360 B2 | 6/2003 | Francischelli |
| 6,585,732 B2 | 7/2003 | Mulier |
| 6,610,055 B1 | 8/2003 | Swanson et al. |
| 6,610,060 B2 | 8/2003 | Mulier |
| 6,613,048 B2 | 9/2003 | Mulier |
| 6,623,515 B2 | 9/2003 | Mulier et al. |
| 6,645,199 B1 | 11/2003 | Jenkins et al. |
| 6,648,883 B2 | 11/2003 | Francischelli |
| 6,656,175 B2 | 12/2003 | Francischelli |
| 6,663,627 B2 | 12/2003 | Francischelli |
| 6,692,450 B1 | 2/2004 | Coleman |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,807,968 B2 | 10/2004 | Francischelli |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 7,128,740 B2 | 10/2006 | Sie et al. |
| 2002/0019630 A1 | 2/2002 | Falwell et al. |
| 2002/0065515 A1 | 5/2002 | Falwell et al. |
| 2003/0045872 A1 | 3/2003 | Jacobs |
| 2003/0144656 A1 | 7/2003 | Ocel |
| 2003/0191462 A1 | 10/2003 | Jacobs |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0256522 A1 | 11/2005 | Francischelli et al. |
| 2005/0267454 A1 | 12/2005 | Hissong |

| | | |
|---|---|---|
| 2006/0009756 A1 | 1/2006 | Francischelli |
| 2006/0009759 A1 | 1/2006 | Chrisitian |

FOREIGN PATENT DOCUMENTS

| | | |
|---|---|---|
| WO | WO 94/11057 | 5/1994 |

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Techique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594.

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," J of Thorac Cardiovasc Surg, 1991: 101:584-593.

Nardella, "Radio Frequency Energy and Impedance Feedback," SPIE vol. 1068, Catheter Based Sensing and Imaging Technology (1989).

Avitall et al., "A Thoracoscopic Approach to Ablate Atrial Fibrillation Via Linear Radiofrequency Lesion eneration on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889.

Cox et al., "An 8½ Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997:12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

Avitall et al., "The Anatomical Determinants for the Design of Intracardiac Mapping and Ablation Catheters," PACE, vol. 17, May 1994, Part I, pp. 908-918.

Olshansky et al., "Atrial Flutter—Update on Mechanism and Treatment," PACE, vol. 15, Dec. 1992, pp. 2308-2335.

* cited by examiner

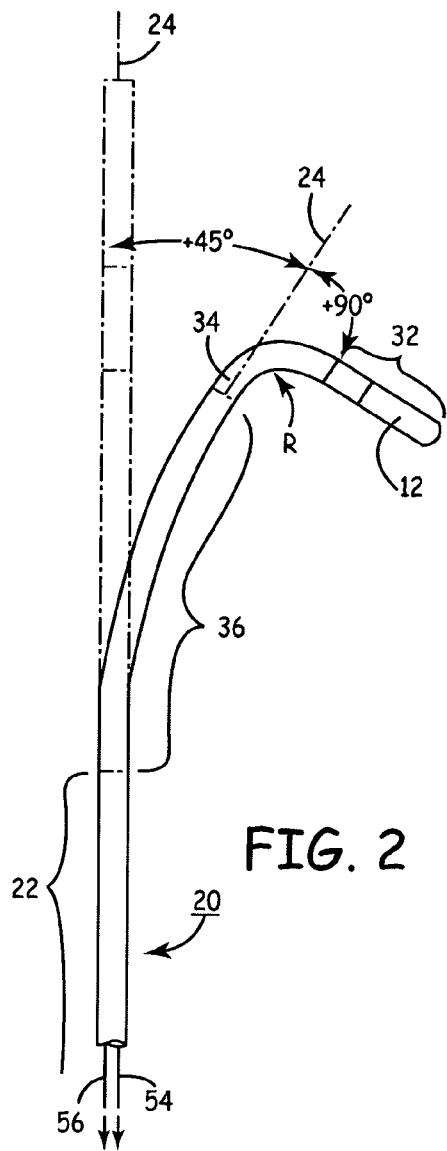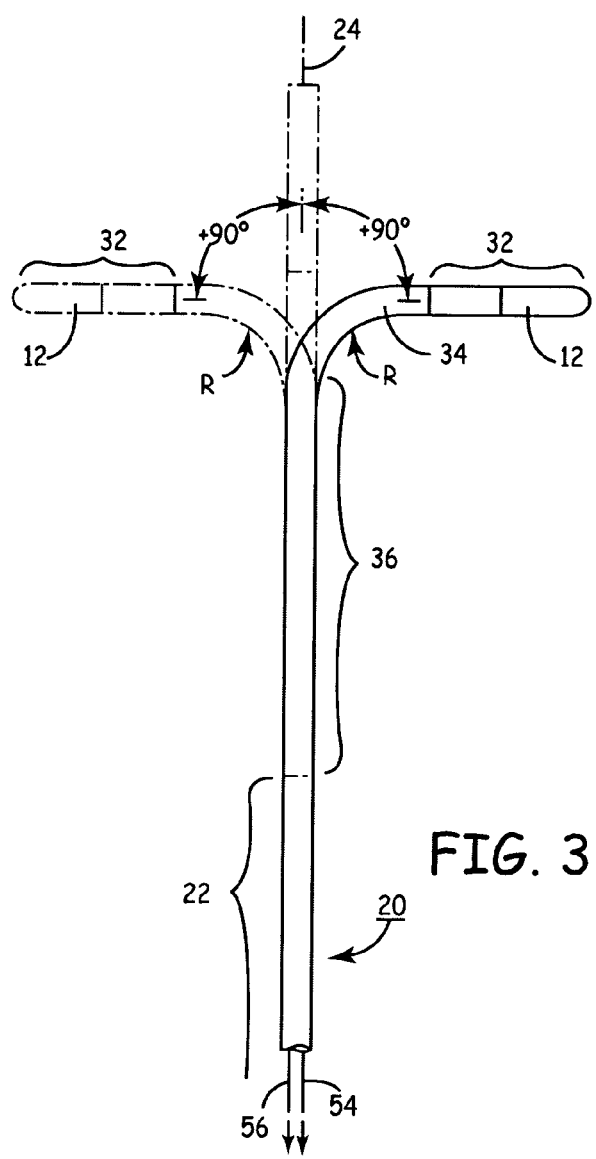

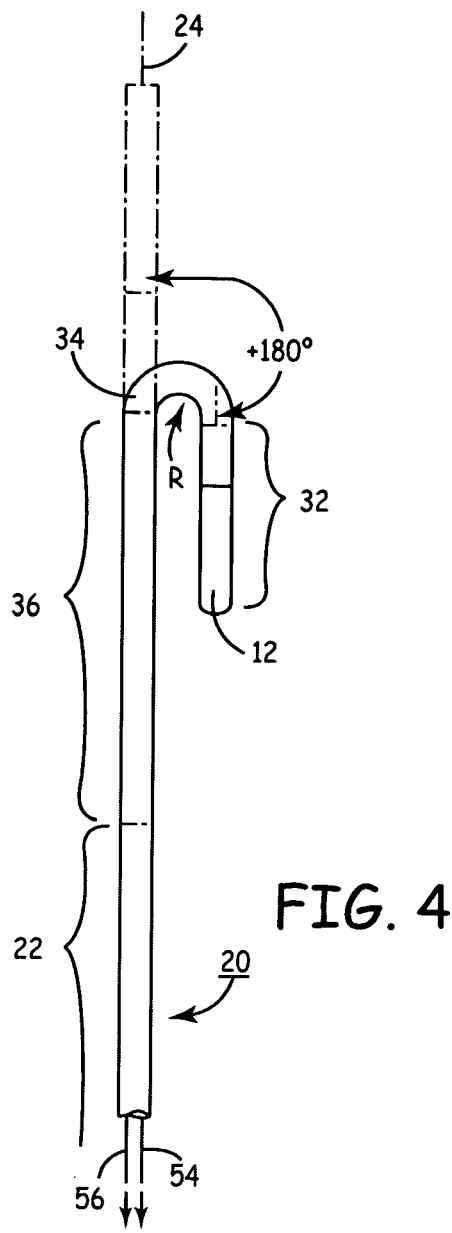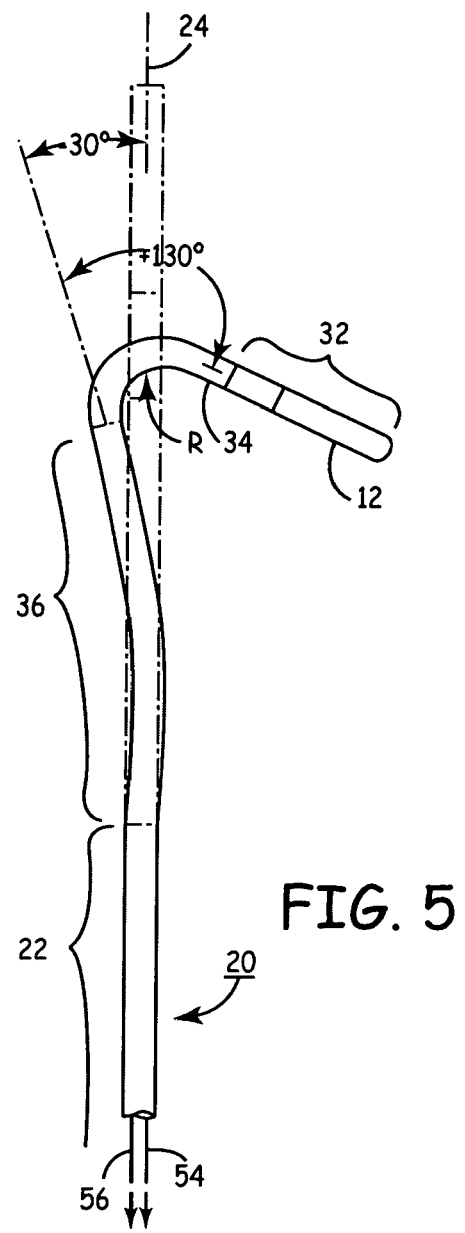
FIG. 4
FIG. 5

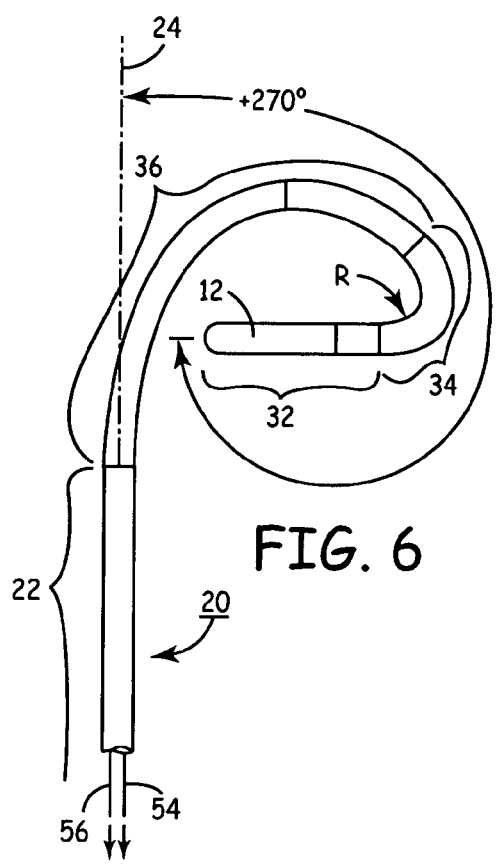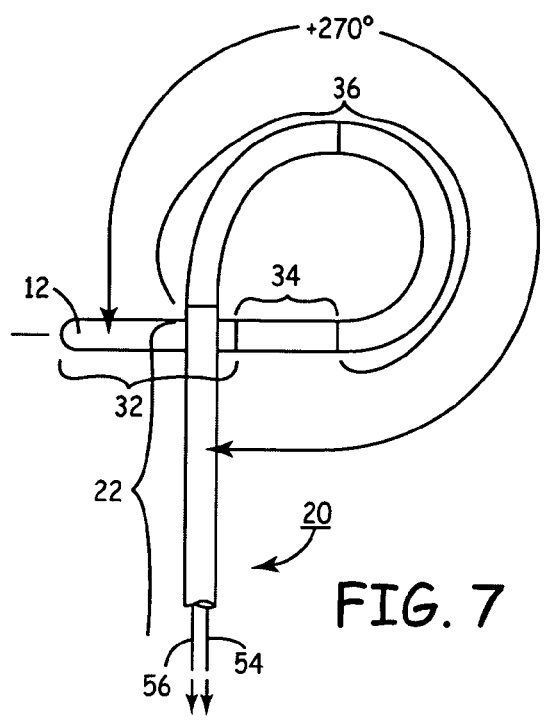
FIG. 6
FIG. 7

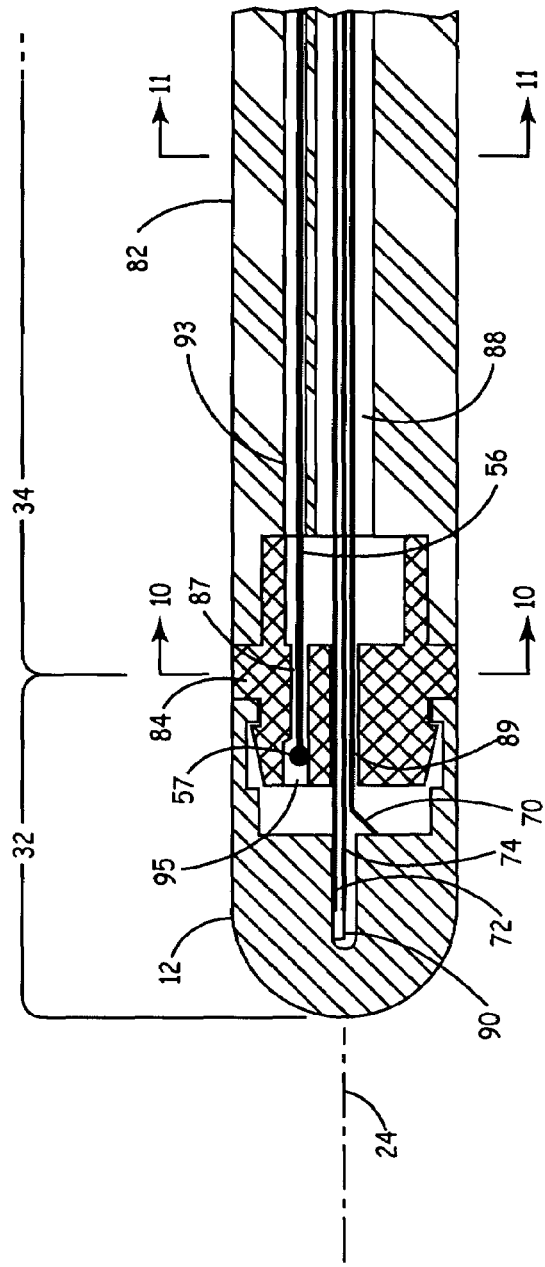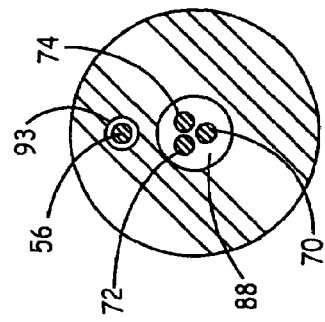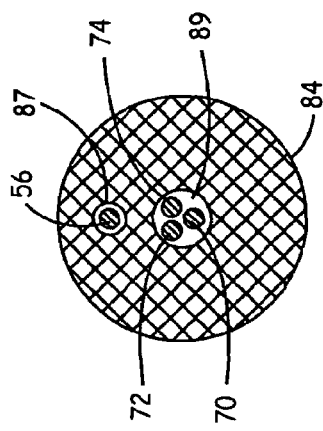

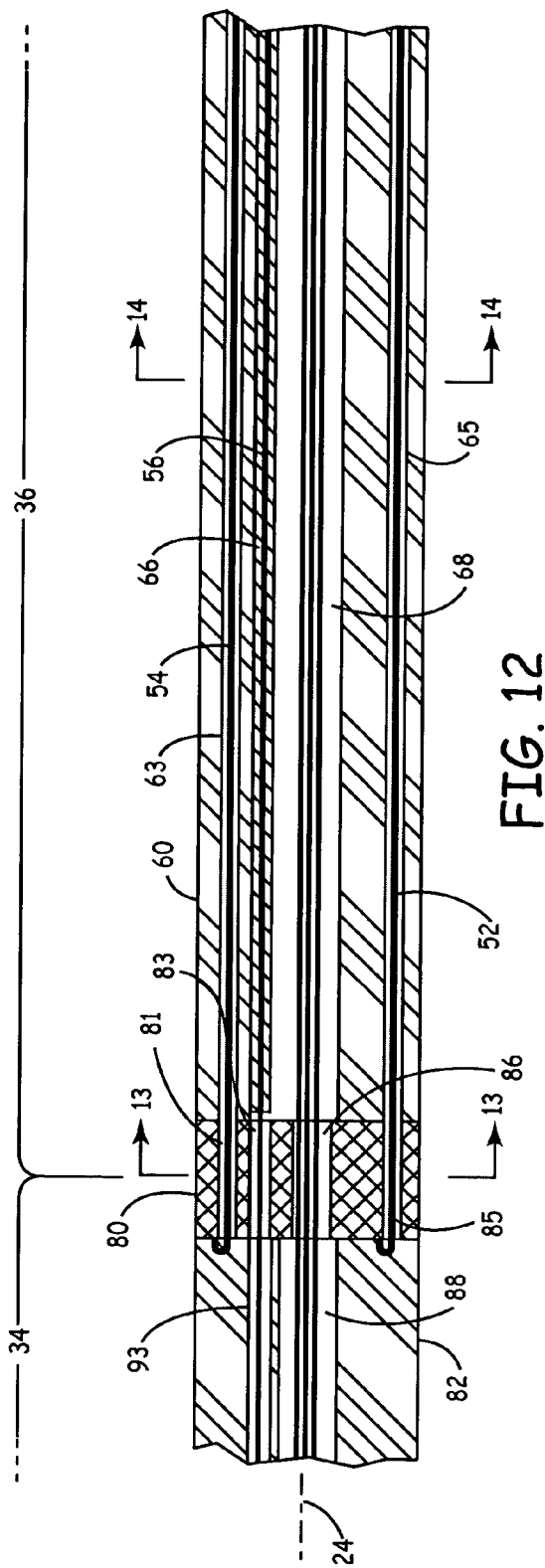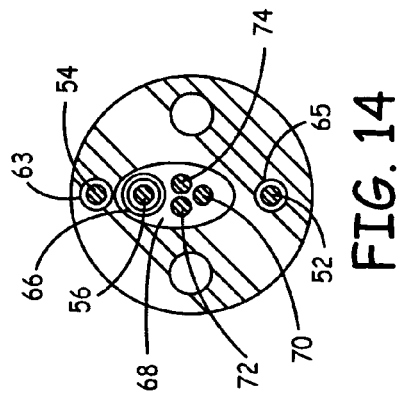

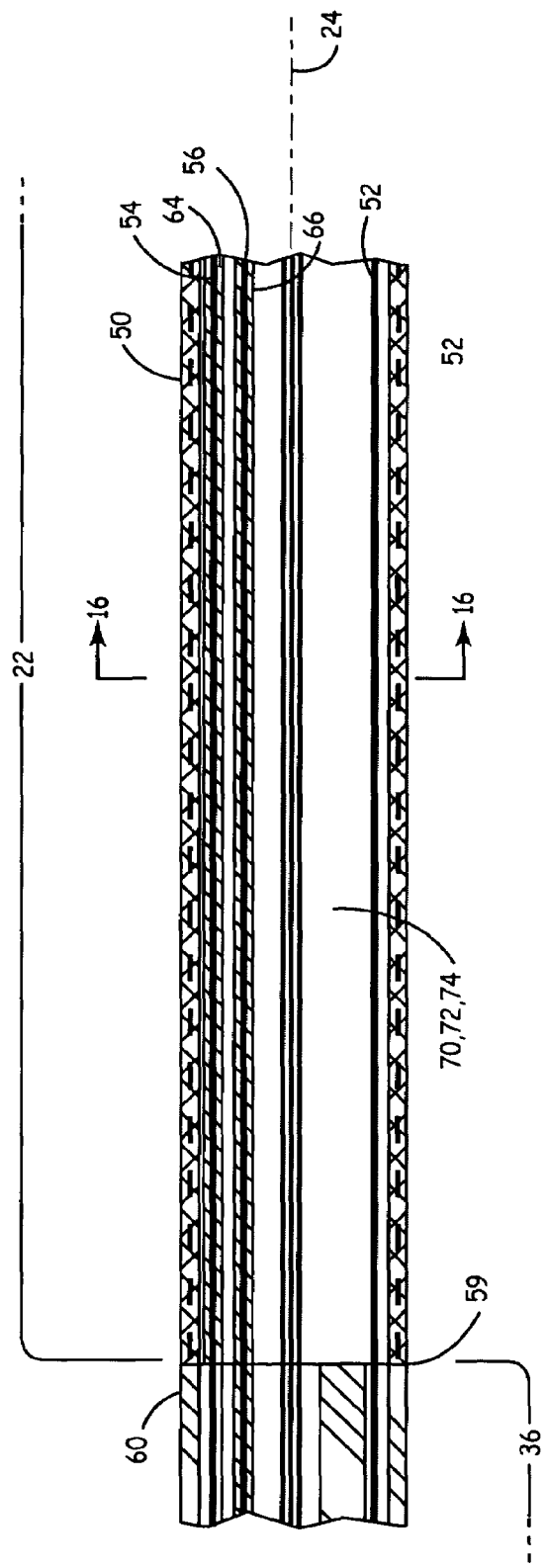
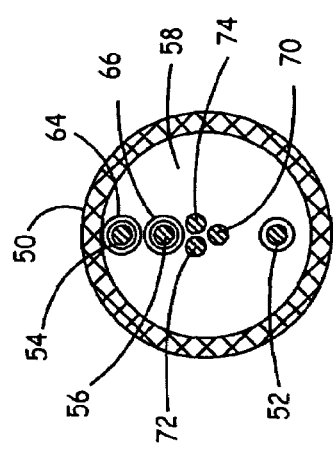
FIG. 15
FIG. 16

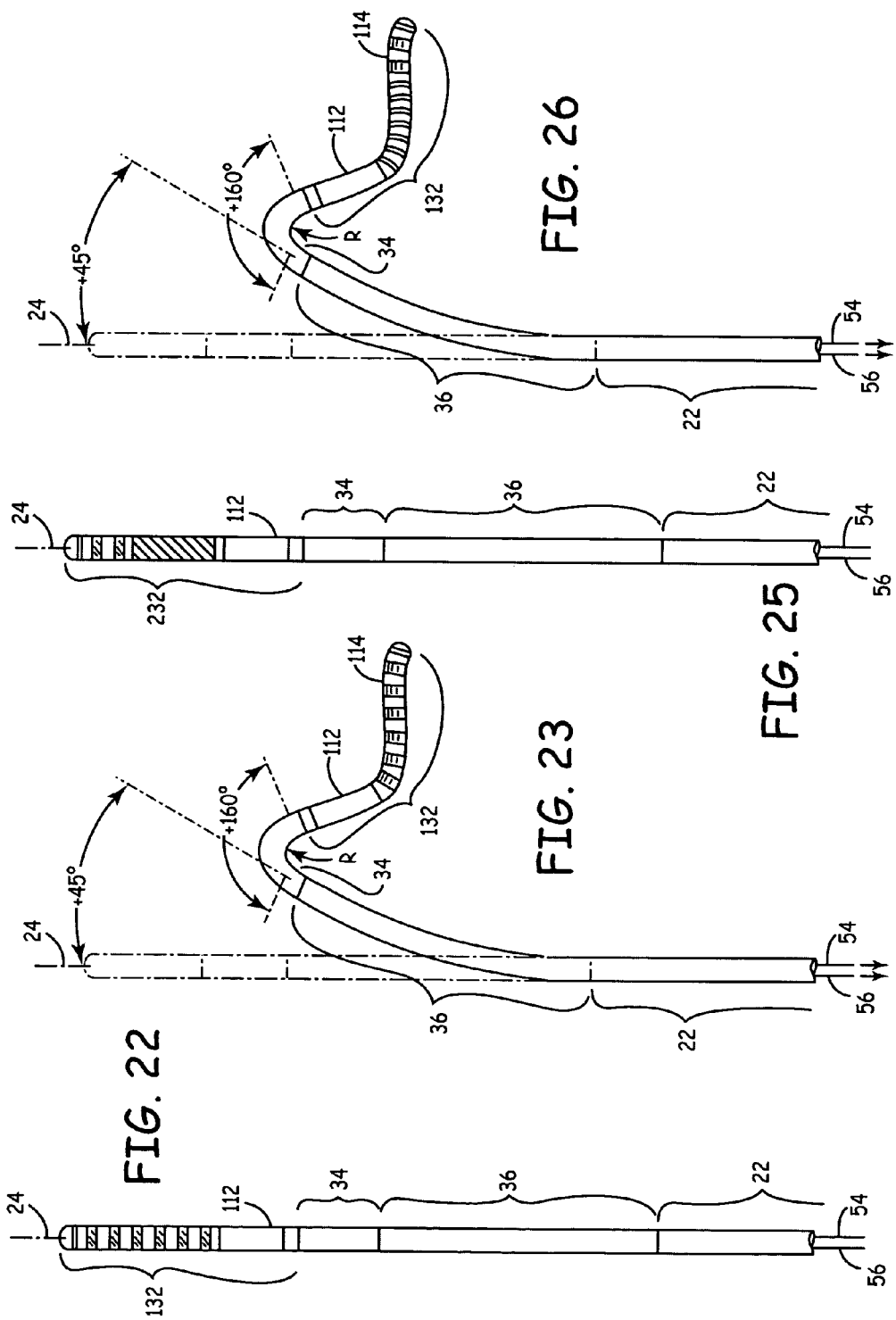

HEART WALL ABLATION/MAPPING CATHETER AND METHOD

FIELD OF THE INVENTION

The present invention relates generally to steerable catheters, and more specifically to steerable electrophysiology catheters for use in mapping and/or ablation of accessory pathways in myocardial tissue of the heart wall.

BACKGROUND OF THE INVENTION

The heart includes a number of pathways through which electrical signals necessary for normal, electrical and mechanical synchronous function or the upper and lower heart chambers propagate. Tachycardia, that is abnormally rapid rhythms of the heart, are caused by the presence of an arrhythmogenic site or accessory pathway which bypasses or short circuits the nodal pathways in the heart. Tachycardias may be categorized as ventricular tachycardias (VTs) or supraventricular tachycardias (SVTs). The most common SVT's include atrioventricular nodal reentrant tachycardia (AVNRT), Atrioventricular reentrant tachycardia (AVRT), atrial fibrillation (AF), and atrial flutter (AF1). Reentrant tachycardias originate in the atria and are typically caused by an accessory pathway or inappropriate premature return excitation from the ventricle through the AV node or left sided accessory pathway. Conditions such as AF and AF1 involve either premature excitation from focal ectopic sites within the atria or excitations coming through inter-atrial reentry pathways as well as regions of slow conduction within the atria. VT's originate from within the ventricles and have their entire circuit contained within the ventricles. These VT's include bundle branch reentrant tachycardia (BBR), right ventricular outflow tract tachycardia (RVOT), and ventricular fibrillation (VF). VT's are often caused by arrhythmogenic sites associated with a prior myocardial infarction as well as reentrant pathways between the ventricles. BBR involves an inappropriate conduction circuit that uses the right and left bundle branches. RVOT can be described as a tachycardia originating from the right ventricular outflow tract which involves ectopic triggering or reentry mechanisms. VF is a life threatening condition where the ventricles entertain a continuous uncoordinated series of contractions that cause a cessation of blood flow from the heart. If normal sinus rhythm is not restored, the condition is terminal.

Treatment of both SVTs and VTs may be accomplished by a variety of approaches, including drugs, surgery, implantable electrical stimulators, and catheter ablation of cardiac tissue of an effected pathway. While drugs may be the treatment of choice for many patients, drugs typically only mask the symptoms and do not cure the underlying cause. Implantable electrical stimulators, e.g., pacemakers, afferant nerve stimulators and cardioverter/defibrillators, usually can only correct an arrhythmia after it occurs and is successfully detected. Surgical and catheter-based treatments, in contrast, will actually cure the problem usually by ablating the abnormal arrhythmogenic tissue or accessory pathway responsible for the tachycardia. The catheter-based treatments rely on the application of various destructive energy sources to the target tissue including direct current electrical energy, radio frequency (RF) electrical energy, laser energy, ultrasound, microwaves, and the like.

RF ablation protocols have proven to be highly effective in treatment of many cardiac arrhythmias while exposing the patient to minimum side effects and risks. RF catheter ablation is generally performed after an initial electrophysiologic (EP) mapping procedure is conducted using an EP mapping catheter to locate the arrhythmogenic sites and accessory pathways. After EP mapping, an RF ablation catheter having a suitable electrode is introduced to the appropriate heart chamber and manipulated so that the electrode lies proximate the target tissue. Such catheters designed for mapping and ablation, frequently include one or more cylindrical or band-shaped individual electrodes mounted to the distal section of the catheter so as to facilitate mapping of a wider area in less time, or to improve access to target sites for ablation. RF energy is then applied through the electrode(s) to the cardiac tissue to ablate a region of the tissue that forms part of the arrhythmogenic site or the accessory pathway.

Ablation of VT's can be difficult due to the thickness of the ventricular chamber walls. Typical RF delivery through standard electrodes is not capable of creating deep transmural lesions in the ventricles. When RF power is raised to high levels, tissue charring and subsurface steam explosions can occur. Coagulum buildup on the electrode surfaces leads to high impedance problems and more importantly, thrombi may be released that could cause stroke. These factors present major problems that limit the safe depth to which lesions can be created. To overcome these problems, saline irrigated electrodes were developed to allow more efficient RF delivery to the myocardium. These irrigated systems nearly eliminate coagulum buildup that would cause impedance rises and increase the risk of stroke. Irrigation keeps the metallic electrodes cool which prevents endocardial surface charring and tissue dessication. With irrigated RF ablation, there remains the problem of creating excessive subsurface temperatures that can lead to steam explosions and cratering of the endocardium.

The following remarks generally apply to catheters designed to perform either one or both of the EP mapping and RF ablation functions, unless otherwise expressly indicated. Illustrative catheters of this type are described in commonly assigned U.S. Pat. Nos. 5,318,525, 5,545,200 and 5,823,955, for example. As described therein, it is frequently desirable to deflect a distal tip section of the catheter body into a non-linear configuration such as a semicircle or curved configuration, which facilitates access to the endocardial heart wall to be mapped or ablated. Such deflection may be accomplished through the use of pull wires secured along the distal tip section which can be tensioned by a control on the handle at the proximal end of the catheter to deflect the tip in the desired configuration. In addition, rotational positioning of the distal tip section is accomplished, either by rotating the entire catheter from the proximal end, or by exerting torque on a core wire secured to the distal tip without rotating the catheter body itself as disclosed in the above-referenced '525 patent. Moreover, selectively retractable stiffening or deflecting core wires are also employed in the design of such catheters as shown in the above-referenced '200 patent for example.

Such mapping and ablation catheters are inserted into a major vein or artery, usually in the neck or groin area, and guided into the chambers of the heart by appropriate manipulation through the vein or artery. The catheter must have a great deal of flexibility or steerability to be advanced through the vascular system into a chamber of the heart, and the catheter must permit user manipulation of the tip even when the catheter body traverses a curved and twisted vascular access pathway. Such catheters must facilitate manipulation of the distal tip so that the distal electrode(s) can be positioned and held against the tissue region to be mapped or ablated.

While EP mapping and RF ablation catheters having the aforementioned deflectability and steerability have had promising results, such catheters suffer from certain disadvantages. The catheters disclosed in the '200 patent provide a continuous curve of the distal tip section having a selectable radius so that the plurality of ring-shaped electrodes are distributed in a desired curved to bear against the heart wall at certain sites. The above-referenced, commonly assigned '200 and '955 patents have at least two segments in the distal tip section of the catheter body that are independently variable. The '955 patent discloses a curvature of the proximal segment of the distal section in one direction, and the distal segment of the distal section in the opposite direction but in the same plane as the proximal segment. The '955 patent distal tip section configuration is particularly adapted for mapping and ablation of tissues around the right and left heart atrioventricular (AV) valve annulus. The '200 patent also discloses a curvature of the distal segment of the distal section in a lateral direction, out of the plane of the curvature established independently in the proximal segment of the distal section. The degree of deflection of the distal segment with respect to the proximal segment is limited, and the curves that can be obtained in the distal segment are limited. Moreover, the limited curvature or angular displacement of the distal segment with respect to the proximal segment and the proximal section of the catheter body does not make it possible to optimally apply the distal tip electrode(s) against other target points or sites of the heart wall or endocardium.

A steerable catheter for mapping and/or ablation is needed that enables mapping and ablation about a variety of structures of the heart comprising particularly about various vascular orifices or valves entering the right and left atria and the valves between the atria and ventricles.

Furthermore, there is a need for a catheter having the capability of abruptly changing the angle of the tip electrode(s) bearing segment with respect to the more proximal catheter shaft in order to enable full length tissue contact of the side of an elongated electrode or set of electrodes with the heart tissue to be mapped or ablated.

SUMMARY OF THE INVENTION

The present invention is directed to a steerable catheter for mapping and/or ablation that comprises a catheter body having a proximal section and a distal section, a handle coupled to he proximal end of the catheter body, and manipulators that enable the deflection of a distal segment of the distal tip section with respect to a proximal segment of the distal tip section or the proximal section. The manipulators enable independently imparting a curvature of the proximal segment and a bending or knuckle motion of an intermediate segment between the proximal and distal segments. A wide angular range of deflection within a very small knuckle curve or bend radius in the intermediate segment is obtained. At least one distal tip electrode is preferably confined to the distal segment which can have a straight distal segment axis or can have a pre-formed curvature of the distal segment axis extending distally from the intermediate segment.

The manipulators preferably comprise a proximal curve forming pull wire and a knuckle bend forming pull wire extending from manipulator elements of the handle to the proximal and intermediate segments that enable independently forming the curvature in the proximal segment and knuckle bend in the intermediate segment in the same direction and in the same plane. The axial alignment of the distal segment with respect to the axis of the proximal shaft section of the catheter body can be varied by pulling proximally on the knuckle bend forming pull wire between substantially axially aligned (0°) to a substantially side-by-side alignment accomplished by a substantially +180° bending curvature of the intermediate segment within a bending radius of between 2.0 mm and 7.0 mm and preferably less than 5.0 mm. The possible range of positive curvature of the proximal segment with respect to the catheter body axis (0° reference) is to about +270° when the proximal curve forming pull wire is pulled proximally.

Alternatively, the manipulators preferably comprise a proximal curve forming push-pull wire and/or a knuckle bend forming push-pull wire extending from manipulator elements of the handle to the proximal and intermediate segments that enable independently forming the curvature in the proximal segment and knuckle bend in the intermediate segment in the same or opposite directions direction but in the same plane. The axial alignment of the distal segment with respect to the axis of the proximal shaft section of the catheter body can be varied by pushing distally on the knuckle bend forming pull wire. By pushing, an abrupt knuckle bend can be formed in the intermediate segment ranging from substantially 0° to about −90° within the bending radius of between 2.0 mm and 7.0 mm and preferably less than 5.0 mm. Similarly, a negative curvature can be formed in the proximal segment by pushing the proximal curve forming push-pull wire. The possible range of curvature of the proximal segment with respect to the catheter body axis (0° reference) is to substantially −90° when the push-pull wire is pushed distally.

In one preferred embodiment, the pull wires or push-pull wires traverse lumens in the catheter body that are offset from the catheter body axis in a common radial direction so that the positive curve formed in the proximal segment and the knuckle bend formed in the intermediate segment are in the same direction.

The ranges of knuckle bend and proximal segment curvature can be limited during manufacture by selection of range of movement of the manipulator elements of the handle to provide desirable deflections to optimally access particular sites of the heart for mapping or ablation. The independently formed curvature of the proximal segment and small radius knuckle bend of the intermediate segment provides a wide variety of optimal configurations for making firm contact with certain sites of ectopic foci, arrhythmia sustaining substrates or accessory pathways of interest in the heart. These sites include those adjacent to the Eustachian ridge, the AV node, the triangle of Koch in the right atrium, those encircling the orifices of the pulmonary veins in the left atrium, and those accessed under the cusps of the mitral valve in the left ventricle.

In a further preferred embodiment, the distal segment of the distal section of the catheter body is configured to elastically conform to the septal wall extending from the Eustachian ridge to the tricuspid valve annulus including the caval-tricuspid isthmus when a knuckle bend is formed in the intermediate segment that hooks over the Eustachian ridge at the orifice of the inferior vena cava. In this embodiment, the proximal segment and proximal segment manipulators can be eliminated or not employed.

The curvature of the proximal segment and the bending angle of the intermediate segment are independently selectable by the physician by independently operating the separate manipulators. Thus, when a suitable bend or curvature is formed in the intermediate and proximal segments, it is not unduly affected when the other of the curvature or bend is changed.

BRIEF DESCRIPTION OF THE DRAWINGS

These and other features and advantages of the invention will become apparent from the following description in which the preferred embodiments are disclosed in detail in conjunction with the accompanying drawings in which:

FIGS. 2-7 are simplified views of the distal section of the catheter body of FIG. 1 showing the movement of the proximal, intermediate and distal segments from the straight, dashed line position to the depicted curved positions;

FIG. 9 is a side cross-section view of the junction of the distal and intermediate segments and the intermediate segment tube of the distal section of the catheter body of FIG. 1;

FIG. 10 is an end cross-section view along lines 10-10 of FIG. 9 depicting the internal structure of a distal insulator member at the junction of the distal and intermediate segments of the distal section of the catheter body of FIG. 1;

FIG. 11 is an end cross-section view along lines 11-11 of FIG. 9 depicting the internal structure of the intermediate segment tube of the distal section of the catheter body of FIG. 1;

FIG. 12 is a side cross-section view of the junction of the proximal and intermediate segments and the proximal segment tube of the distal section of the catheter body of FIG. 1;

FIG. 13 is an end cross-section view along lines 13-13 of FIG. 12 depicting the internal structure of a proximal insulator member at the junction of the proximal and intermediate segments of the distal section of the catheter body of FIG. 1;

FIG. 14 is an end cross-section view along lines 14-14 of FIG. 12 depicting the internal structure of the proximal segment tube of the distal section of the catheter body of FIG. 1;

FIG. 15 is a side cross-section view of the junction of the proximal segment with the distal end of the proximal section as well as of the proximal section of the catheter body of FIG. 1;

FIG. 16 is an end cross-section view along lines 16-16 of FIG. 15 depicting the internal structure of the proximal section of the catheter body of FIG. 1;

FIGS. 22 and 23 are simplified views of the distal section of the catheter body of FIG. 21 showing the movement of the proximal, intermediate and distal segments from the straight position to the depicted curved position;

FIGS. 25 and 26 are simplified views of the distal section of the catheter body of FIG. 24 showing the movement of the proximal, intermediate and distal segments from the straight position to the depicted curved position.

DETAILED DESCRIPTION OF THE PREFERRED EMBODIMENTS

Figure 1:
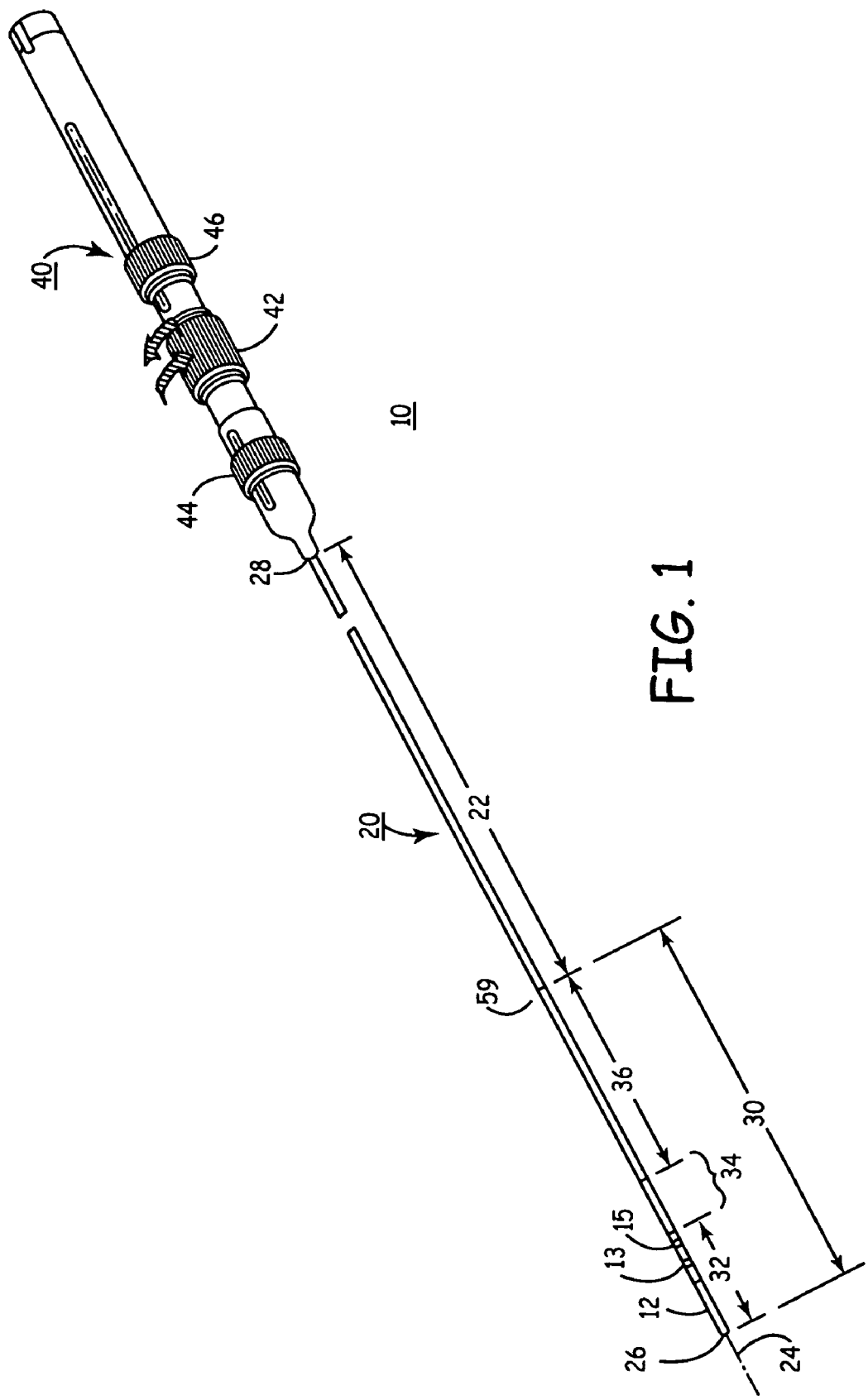
FIG. 1 is an overall view of one embodiment of an ablation and/or EP mapping catheter made according to the invention which can accommodate a variety of electrode configurations.

FIG. 1 schematically illustrates an anatomically-conforming, multi-curve catheter 10 incorporating various features of the present invention for orienting a distal tip electrode 12 (or electrodes) with respect to the heart wall for RF ablation and/or EP mapping. The multi-curve catheter 10 can incorporate a porous tip and catheter lumen for emitting irrigating fluid around the distal tip electrode 12, but those features are not illustrated in FIG. 1 to simplify illustration. Moreover, the distal segment 32 is simplified in FIG. 1 to show an elongated tubular shaped ablation electrode 12 and a pair of mapping electrodes 13 and 15 in the illustration of FIG. 1, but the distal segment 32 may comprise a plurality of ring-shaped electrodes, one or more coil electrode or the like having other shapes that are presently used or may come into use and including several variations described below in reference to other figures. It will be understood that the catheter 10 also represents an ablation catheter construction delivering other forms of ablation energy, including visible or invisible light, infrared, and electrical energy from or along the distal tip.

The catheter 10 comprises a catheter shaft or body 20 and a handle 40. The catheter shaft or body 20 has a shaft axis 24 and extends between a distal end 26 and a proximal end 28 and is separated into a proximal section 22 and a distal section 30. Catheter body 20 may be of any suitable diameter and length and may be straight or pre-curved along its length, but preferably is straight when unrestrained. The distal section 30 or the distal segment thereof can be tapered from the diameter of the proximal section 22. Preferably, the catheter body 20 has a uniform outside diameter of about 0.052 inch (1.32 mm) to 0.1040 inch (2.64 mm) and a length of about 50 cm to 110 cm.

The proximal section 22 has sufficient column strength and is capable of good torque transmission to permit controlled placement of the distal section 30 at a target site in the heart including a selected cardiac valve or vessel in the manners discussed below. The distal section 30 is deflectable away from shaft axis 24 and includes a distal segment 32, a curvable proximal segment 36 having a proximal segment length, and a bendable intermediate segment 34 having an intermediate segment length disposed between the distal segment 32 and the curvable proximal segment 36. The illustrative tip electrode 12 is positioned along the distal segment 32, preferably extending proximally from the catheter body distal end 26 through all or part of the length of the distal segment 32. The distal segment 32 can include an elongated ablation electrode 12 that may be solid or irrigated and can include one or more proximal ring electrodes 13, 15 for use in mapping that are either located proximally as shown or distally from ablation electrode 12. Each electrode is separately connected to insulated conductors extending proximally through the catheter body 20 to terminals of a cable connector in or on the handle 40 that is connected via a cable to the ablation energy source and/or mapping signal amplifiers. As described further below, a thermocouple is also typically included in the distal segment 32 of such ablation catheters, and separately insulated thermocouple conductors extending proximally through the catheter body 20 to terminals of the cable connector in or on the handle 40 that are coupled via a cable to the temperature display and ablation energy control apparatus known in the art.

The handle 40 can take any of the forms known in the art for making electrical connections with the conductors within the catheter body 20, for delivering irrigation fluid to an irrigation lumen (if present) of the catheter body 20. The handle 40 also comprises a mechanism for deflecting the distal tip section 30 into the shapes provided by the present invention. The mechanism can take any form for pulling, pushing and/or twisting the deflection or push/pull wires within the catheter body 20 as described further below. In the illustrated embodiment, the handle 40 is attached to the catheter body proximal end 28 and supports axially slidable manipulators comprising push-pull rings 44 and 46 and a rotatable lateral deflection ring 42 that are coupled to the proximal ends of a curve deflection push-pull wire, a knuckle deflection push-pull wire, and a lateral deflection wire identified and described further below. The lateral deflection ring 42 can be rotated to impart a torque in a lateral deflection wire coupled thereto to laterally rotate the distal section 30 with respect to axis 24 within the proximal section 22. The details of construction of one embodiment of the components of the catheter body 20 are set forth in FIGS. 8-16 and these curve and rotation functions are described further below.

As shown in FIG. 1, when the push-pull wires are relaxed, the distal segment 32, the bendable intermediate segment 34, and the curvable proximal segment 36 are aligned with the shaft axis 24 which is referenced as 0°. The knuckle deflection push-pull wire can be retracted or pulled by sliding ring 46 proximally to impart a small radius bend from substantially 0°, wherein the distal and proximal segments 32 and 36 are axially aligned, to substantially 180°, whereby the distal and proximal segments 32 and 36 are substantially in side-by-side alignment. The knuckle deflection push-pull wire can be extended or pushed by sliding push-pull ring 46 distally to impart a small radius bend from substantially 0° to about −90°, that is in a bend direction opposite to the bend direction imparted when the knuckle deflection push-pull wire is retracted or pulled by sliding ring 46 proximally. The intermediate segment 34 is bent in a bending radius of between 2.0 mm and 7.0 mm, and preferably less than about 5.0 mm within the bending angle range. The abrupt knuckle bend angle range can be restricted further by positioning of the slide end stops for the push-pull ring 46 during assembly.

The manipulator push-pull ring 44 can be moved proximally or distally to move the curve deflection push-pull wire coupled thereto proximally or distally to form a curve in the proximal segment 36 that is opposed to or in the same direction as the bend imparted in the intermediate segment 34. The bend or curve of the proximal segment 36 that can be induced relative to the catheter body axis 24 as depicted in the figures can be between −90° to +270° relative to the proximal section 22. The curvature range of the proximal segment 36 can be restricted further by position of the slide end stops for the push-pull ring 44 during assembly.

FIGS. 2 through 7 illustrate four of many possible co-planar curves induced in the segments of the distal section 30 in relation to the catheter body axis 24 accomplished by selective movement of the axially slidable manipulator rings 46 and 44 coupled to the knuckle deflection push-pull wire 56 and the curve deflection push-pull wire 54, respectively. The distal end of the knuckle deflection push-pull wire 56 terminates at the junction of the intermediate segment 34 with the distal segment 32, and the curve deflection push-pull wire 54 terminates at the junction of the intermediate segment 34 with the proximal segment 36. The knuckle deflection push-pull wire 56 and the curve deflection push-pull wire 54 extend in parallel with and are radially aligned to the catheter body axis 24 along a common radius extending from the catheter body axis 24 through the proximal section 22 and the proximal segment 36. The knuckle deflection push-pull wire 56 is spaced further away from the axis 24 than the curve deflection push-pull wire 54 through the proximal section 22 and proximal segment 36. The distal section of the knuckle deflection push-pull wire 56 traversing the intermediate segment 34 is axially aligned with the axis of the curve deflection push-pull wire 54 in the proximal segment 36.

In FIG. 2, both the knuckle deflection push-pull wire 56 and the curve deflection push-pull wire 54 are pulled proximally to induce a short radius, 90° knuckle bend in the intermediate segment 34 and a long radius curve in the same plane and direction in the proximal segment 36. A 90° bend of the intermediate segment 34 with respect to the proximal shaft section 22 provides an optimum angular orientation of the distal electrode 12 for pushing or pulling it against the heart wall.

FIG. 3 illustrates the same short radius, 90° knuckle bend formed in the intermediate segment 34 but without any curvature formed in the proximal segment 36. As set forth above, a knuckle bending radius between 2.0 mm and 7.0 mm and preferably less than about 5.0 mm is provided.

FIG. 4 illustrates the full substantially 180° knuckle bend formed in the intermediate segment 34 without any curvature formed in the proximal segment 36, so that the distal and proximal segments 32 and 36 are substantially in side-by-side orientation.

The curve deflection push-pull wire 54 can be both pulled proximally as shown in FIG. 2 to induce a curvature in the same direction as the knuckle bend in intermediate segment 34 and pushed distally as shown in FIG. 5 to induce a curvature in the opposite direction as the knuckle bend in intermediate segment 34. The curvature that can be induced in the proximal section ranges from −90° to +270° relative to the proximal section 22 and with respect to catheter body straight axis 24, but smaller ranges can be selected.

FIG. 6 illustrates a +270° curvature in the distal section 22 effected by retraction of both push-pull wires 54 and 56, and FIG. 7 illustrates a +270° curvature in the distal section 22 effected by retraction of only curve deflection push-pull wire 5. In this way, the distal electrode 12 is positioned at −90° to the proximal section 22, which is a useful orientation for ablating or mapping the heart wall at the caval-tricuspid isthmus or sites under in the ventricles the mitral or tricuspid valve flaps.

The lateral deflection that can also be induced to orient the distal tip electrode 12 out of the plane of FIGS. 2-7 using the lateral deflection wire 52 and manipulator ring 42 is not shown in these figures since it would be out of the plane of the paper that the drawings are printed on. When the ring 42 is rotated clockwise or counterclockwise, the lateral deflection wire is twisted, causing the junction of the proximal and intermediate segments 36 and 34 to rotate. It will be understood from the construction of the lateral deflection wire described below that a lateral deflection of the tip segment 32 and the intermediate segment 34 in the range of −90° to +90° with respect to catheter body straight axis 24 can be achieved by such rotation.

The structure of the catheter body 20 that achieves these angular tip section deflections and the lateral deflection is illustrated in FIGS. 8-16. FIGS. 9-16 also show the internal arrangement of the pull wires and wire lumens as well as the wires that apply RF energy to the tip electrode 12 and a thermocouple located in a cavity in the tip electrode 12.

Figure 8:
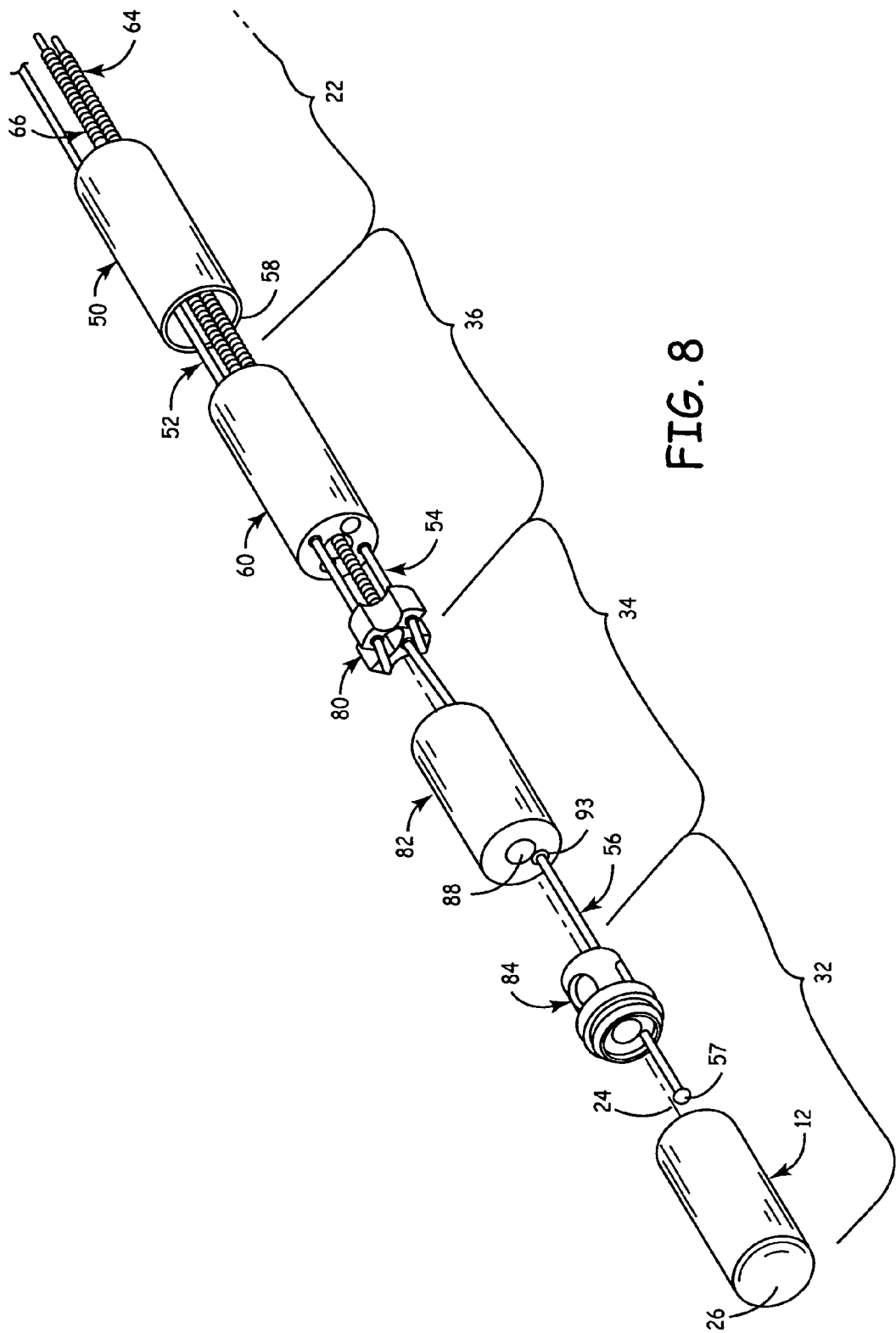
FIG. 8 is an exploded perspective view of the principal components of the catheter body of FIG. 1.

The proximal section 22 shown in FIGS. 8 and 15-16, is formed of an outer shaft jacket or sheath 50, preferably made of high durometer (such as 72D) Pebax® reinforced by a braided wire tubing formed of flat, stainless steel wire embedded within the sheath wall that encloses a sheath lumen 58. Pebax® polyamide polyether block copolymer is made by Elf Atochem, Inc. of Philadelphia, Pa. The sheath lumen 58 encloses the knuckle deflection push-pull wire 56, the curve deflection push-pull wire 54, and the lateral deflection wire 52. The sheath lumen 58 also receives the distal tip electrode conductor 70 extending between the handle 40 and the distal tip electrode 12 and thermocouple wires 72 and 74 that extend between a thermocouple 90 (depicted in FIG. 9) and temperature monitoring circuitry of the RF energy generator. The thermocouple 90 provides temperature readings to modulate the delivered energy level or duty cycle to avoid undue heating of the distal tip electrode 12 during ablation. The distal tip electrode conductor 70 is used to convey electrical signals of the heart sensed through the tip electrode 12 to ECG display equipment coupled to a terminal of the handle 40 during EP mapping or to deliver the RF energy from the RF energy generator to the distal tip electrode 12. These conductors 70, 72 and 74 would be separately electrically insulated from one another and the knuckle deflection push-pull wire 56, the curve deflection push-pull wire 54, and the lateral deflection wire 52. It will be understood that the lumen 58 can be configured with a fluid conduit to direct irrigation fluid to irrigation ports of the distal tip electrode 12 and can be used to carry further wires coupled to additional, more proximally or more distally located, EP mapping and/or ablation electrodes than electrode 12.

The knuckle deflection push-pull wire 56 and the curve deflection push-pull wire 54 are encased within incompressible spiral wire tubes 66 and 64, respectively, that extend from proximal tube ends abutting a stop plate within the distal end of handle 40 distally through the proximal sheath lumen 58. A distal section of the incompressible spiral wire tube 66 and knuckle deflection push-pull wire 56 extends distally from junction 59 of the proximal section 22 and proximal segment 36 through a lumen 68 of proximal segment tube 60. The distal end of the incompressible spiral wire tube 66 is located abutting the proximal insulator 80 shown in FIGS. 8, 12 and 13 that the knuckle deflection push-pull wire 56 passes through, and it is adhered to the proximal insulator 80 when the proximal insulator is thermally bonded between the tubes 60 and 82. The incompressible spiral wire tube 66 is not attached at its proximal end to the handle 40, and it therefore "floats" over the proximal portion of the knuckle deflection push-pull wire 56 that traverses the catheter body proximal section 22 and the proximal section 36 of the distal section 30. This floating feature advantageously prevents the stretching of the coil turns of the incompressible spiral wire tube 64 when the knuckle deflection push-pull wire 56 is pushed or when the adjacent curve deflection push-pull wire 54 is pushed distally or pulled proximally, inducing a curve in the proximal segment 36.

The distal end of the incompressible spiral wire tube 64 is located at the junction 59 of the distal end of proximal sheath 50 with the proximal end of the multi-lumen tube 60 of the proximal segment 36 shown in FIGS. 8 and 15. The junction 59 is a butt welded junction of the distal end of proximal sheath 50 with the proximal end of the multi-lumen tube 60, and so the distal end of the incompressible spiral wire tube 66 is affixed to junction 59 by the solidification of the melted material to it. But, the proximal end of the incompressible spiral wire tube 66 is not attached to the handle 40, so that the coil turns of the incompressible spiral wire tube 66 when the curve deflection push-pull wire 54 is pushed or when the adjacent knuckle deflection push-pull wire 56 is pushed distally or pulled proximally, inducing a curve in the intermediate segment 34.

The incompressible spiral wire tubes 64 and 66 are preferably formed of stainless steel flat wire wound so that the narrow wire edges abut one another in each turn, but do not overlap one another when the coils are compressed by pulling proximally on the curve deflection push-pull wire 54 and the knuckle bend push-pull wire 56. The coil turns of coils formed of circular cross-section wire tends to ride over one another. Preferably, the incompressible spiral wire 64 is 0.017 inches thick by 0.023 inches wide, and the incompressible spiral wire 66 is 0.013 inches thick by 0.019 inches wide. The coil turns are close wound so that the thinner wire sides of each coil turn abut or nearly abut one another.

The knuckle deflection push-pull wire 56 is formed of a nickel-titanium superelastic metal that has a straight memory shape and does not readily kink, enabling the repeated formation of small radius knuckle bends in the intermediate segment 34 as described further below. The curve deflection push-pull wire 54 and the lateral deflection wire 52 are formed of stainless steel, and their distal ends are both attached to the proximal insulator member 80. The lateral deflection wire 52 is tapered and is reduced in diameter distally when it traverses the proximal segment 36. Wires 52, 54 and 56 are preferably coated with a lubricious material, e.g. PTFE or Parylene, to reduce sliding friction.

As shown in FIG. 8, the distal section 30 is formed of the distal electrode 12 and distal insulator 84 together forming the distal segment 32. The intermediate segment 34 is formed of the two-lumen intermediate tube 82 and includes the distal section of knuckle deflection push-pull wire 54. The proximal segment 36 is formed of the multi-lumen tube 60 and proximal insulator 80 along with the wires passing through their lumens. The multi-lumen tube 60 is preferably formed of intermediate durometer (such as 55D) Pebax® polyamide polyether block copolymer. The proximal insulator 80 illustrated in cross-section in FIGS. 12 and 13 is formed of a relatively rigid PEEK (polyether-ether-ketone) or other hard, temperature-resistant material with a number of lumens 81, 83, 85 and 86 extending through it aligned axially with the lumens 63, 65 and 68 of multi-lumen tube 60 and lumens 88 and 93 of two-lumen intermediate tube 82.

The proximal end of the multi-lumen tube 60 is butt welded to the distal end of proximal sheath 50 at the junction 59 as described above and the various conductors and wires are directed through the lumens 63, 65 and 68 as shown in FIG. 14. The knuckle deflection push-pull wire 56 and incompressible spiral wire 66 are directed through elliptical lumen 68 along with the conductors 70, 72 and 74. The incompressible spiral wire 66 terminates in abutment against the proximal insulator 80, but the knuckle deflection push-pull wire extends distally through the proximal insulator 80. The curve deflection push-pull wire 54 is extended distally through the lumen 63 to an attachment with the proximal insulator 80, but the distal end of the incompressible spiral wire 64 is terminated at junction 59 as described above. The lateral deflection wire 52 extends distally through lumen 65 to a connection with the proximal insulator 80. Additional lumens can also be provided in tube 60 that make the tube 60 more flexible and easier to bend.

The two-lumen intermediate tube 82 is preferably formed of relatively soft durometer (such as 35D) Pebax® polyamide polyether block copolymer. The conductors 70, 72 and 74 pass through the central lumen 86 and into a lumen 88 of the two-lumen intermediate tube 82. The knuckle deflection push-pull wire 56 extends distally through lumen 83 of the proximal insulator 80. The curve deflection push-pull wire 54 within lumen 68 extends distally through the lumen 81 where its distal end is bent over and attached to the distal surface of the proximal insulator 80. Similarly, the lateral deflection wire 52 in lumen 65 extends distally through lumen 85 where its distal end is bent over and attached to the distal surface of the proximal insulator 80.

During manufacture, the lumens 93 and 88 of the two-lumen intermediate tube 82 are aligned with the lumens 83 and 86, respectively, of proximal insulator 80 as shown in FIGS. 11 and 13 which are aligned with the central lumen 68 of the multi-lumen tube 60 and the wires are passed through them as described above. The lumens 63 and 65 of the multi-lumen tube 60 are aligned with the lumens 81 and 85 of proximal insulator 80, and the wires 54 and 52 are passed through the aligned lumens as described above. Heat and pressure are applied to the assembly to fuse the proximal insulator 80 between the proximal end of the two lumen intermediate tube 82 and the distal end of the multi-lumen proximal tube 60. The applied heat causes the tube material to flow over scalloped sections of the outer surface of proximal insulator 80 thereby fusing the proximal end of the two lumen intermediate tube 82 with the distal end of the multi-lumen proximal tube 60.

The distal insulator 84 illustrated in cross-section in FIGS. 9 and 10 is formed of a relatively rigid PEEK or other hard, temperature-resistant material and is attached between tube 82 and distal tip electrode 12 preferably using a mechanical interlock and/or adhesive. The distal end of two lumen intermediate tube 82 is shaped to fit over and be adhered through the use of appropriated adhesive, thermal bond, or other appropriate methods to the proximal end of the distal insulator 84 after aligning the lumen 93 with the lumen 87 of distal insulator 84. The conductors 70, 72 and 74 pass through the central lumen 88 of the two-lumen intermediate tube 82 and through a central lumen 89 of the distal insulator 84 as shown in FIGS. 9-11. The distal end of the distal insulator 84 extending through lumen 89 is attached to the distal tip electrode 12 as shown in FIG. 9, and the conductor 70 is butt welded to the distal tip electrode 12. The distal ends of the thermocouple conductors 72 and 74 extend through lumen 89 and are attached to the thermocouple 90 positioned within a cavity of the distal tip electrode 12 as shown in FIG. 14. The knuckle deflection push-pull wire 56 extends distally through lumen 87 of the distal insulator 84. The enlarged diameter distal ball-tip end 57 of the knuckle bend pull wire 56 fits into a bore 95 of the distal insulator 84 so that the distal end of knuckle bend pull wire 56 is fixed in place.

Figure 17:
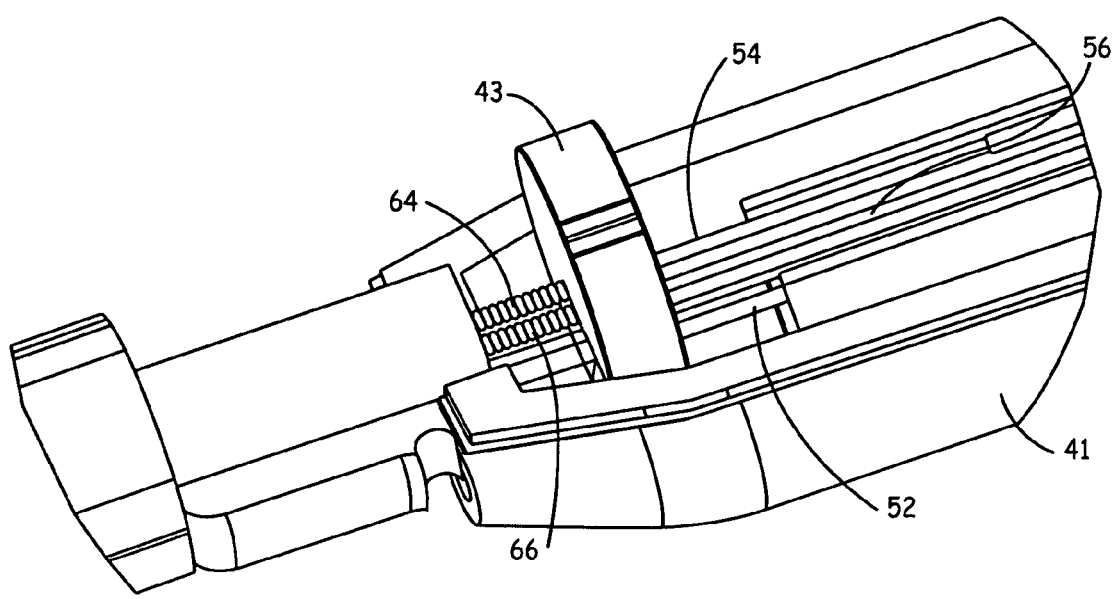
FIG. 17 is a partial perspective view of a frame of the handle depicting the junction of the proximal end of the catheter body with the distal end of the handle showing the proximal ends of the incompressible coils surrounding proximal portions of the knuckle deflection push-pull wire and the curve deflection push-pull wire abutting a disk allowing the incompressible coils to float.

FIG. 17 is a partial perspective view of the distal end of an interior frame member 41 and a coil wire stop plate 43 within the distal end of the handle 40 that is joined with the proximal end of the catheter body 20. FIG. 17 shows that the proximal ends of the incompressible coils 66 and 64 surrounding proximal portions of the knuckle deflection push-pull wire 56 and the curve deflection push-pull wire 54, respectively, simply abut the plate 43. The proximal portions of the knuckle deflection push-pull wire 56, the curve deflection push-pull wire 54, and the lateral deflection wire 52 pass through holes in the plate 43. The incompressible coils 66 and 64 are not otherwise restrained so that the incompressible coils 66 and 64 can move away from the plate 56 and not be stretched if the catheter body 20 is extended distally. In this way, the knuckle deflection push-pull wire 56 and the curve deflection push-pull wire 54 can be extended or pushed distally to impart the negative curvature in the intermediate and proximal segments 34 and 36 without stretching the incompressible coils 66 and 64.

Handle 40 may be of a conventional design, e.g. as shown in the above-referenced, commonly assigned '200 patent, except for the plate 56 and its above described function. Handle 40 also includes an electrical connector connected to electrical conductors 70, 72 and 74 (and any additional conductors) for connection with a cable that is attached to the ECG and/or ablation equipment. Handle 40 may also be configured to be coupled with a source of irrigation fluid if the catheter body 20 and electrode 12 are modified to provide an irrigation fluid lumen and ports through the electrode 12.

Returning to the bendable intermediate segment 34, the relatively flexible tube 82 is thus bounded on its proximal end by the proximal insulator 80 and on its distal end by the distal insulator 84. The length of the tube 82 and the distal section of the knuckle deflection push-pull wire 56 traversing lumen 93 forming the intermediate segment 34 is preferably on the order of about 4.0 mm to 15.0 mm. The length of the tube 60 of the proximal segment 36 is preferably on the order of about 30.0 mm to 120.0 mm.

The proximal segment 36 can be curved as shown in FIGS. 2, 5, 6 and 7 by retraction of the curve deflection push-pull wire 54 by retracting axially slidable manipulator ring 44. The proximal retraction of the knuckle bend pull wire 56 by retracting axially slidable manipulator ring 46 induces a knuckle bend in the tube 82 of the intermediate section 34 as depicted in FIGS. 2-6. independently of the curve induced in the proximal segment 36. The knuckle bend that is induced has a bending radius of less than about 5.0 mm within a bend of substantially 180°.

The incompressible spiral coil wires 64 and 66 prevent the compression of the tube 60 of proximal segment 36 or the sheath 50 of the proximal section 22. The incompressible spiral wires 64 and 66 are not stretched or compressed by retraction of one or another of the push-pull wire 54 or the knuckle bend pull wire 56 or twisting induced by manipulation of the lateral deflection wire 52 because the proximal ends of the incompressible spiral wires 64 and 66 are not attached at the handle 40.

Figure 18:
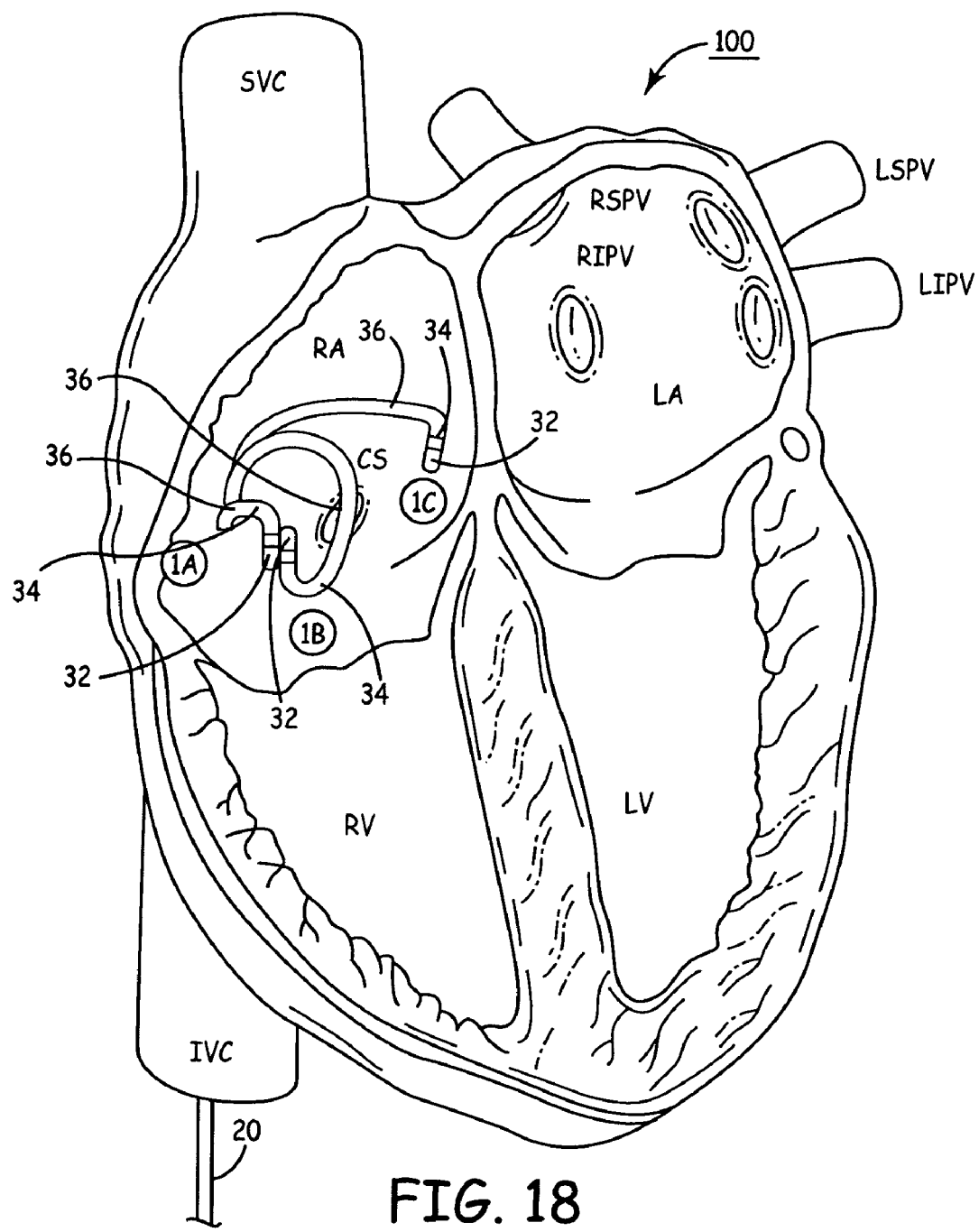
FIGS. 18-20 are schematic illustrations of the selective locations of the distal section of the catheter of FIG. 1 for cardiac mapping and/or ablation.
Figure 19:
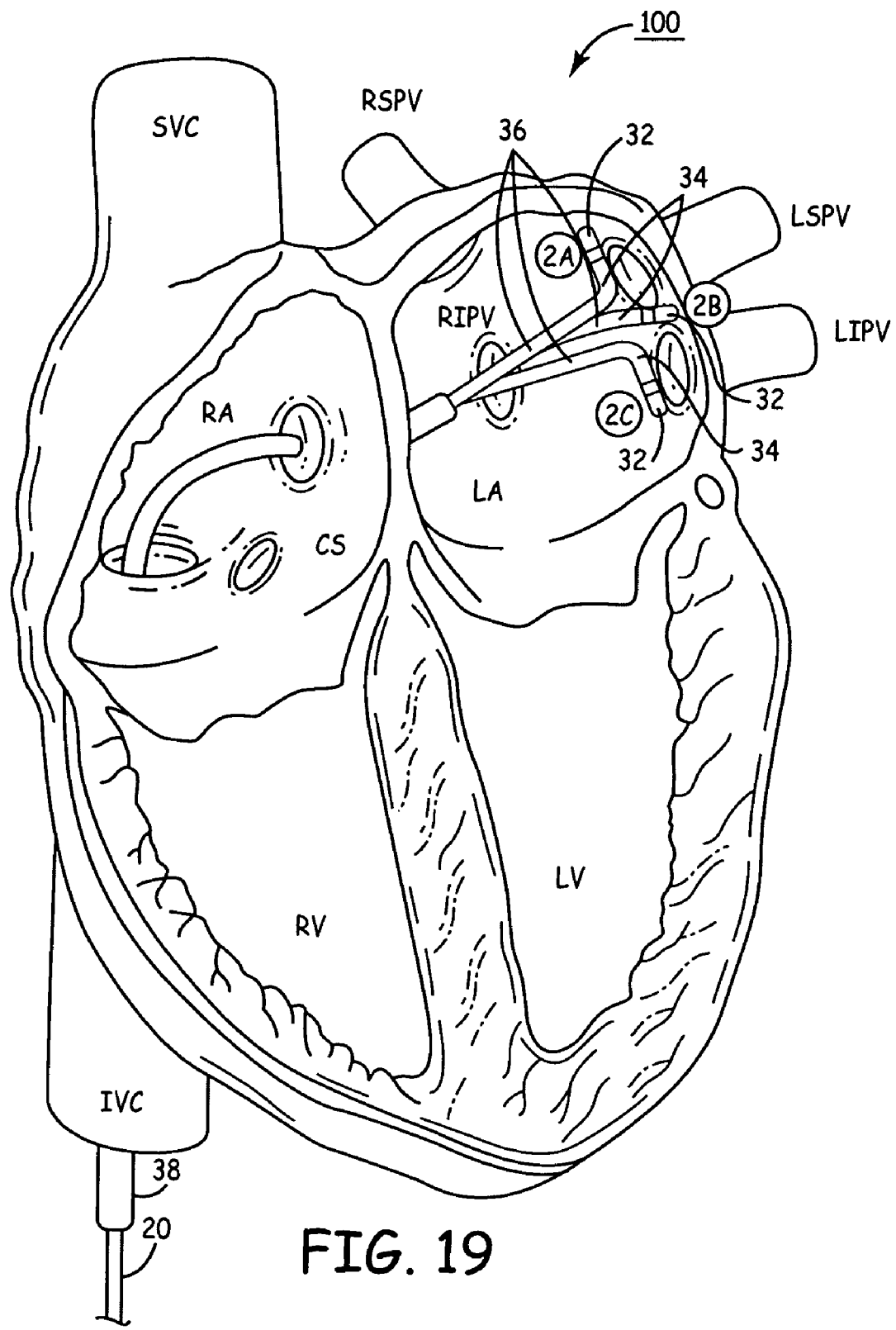
Figure 20:
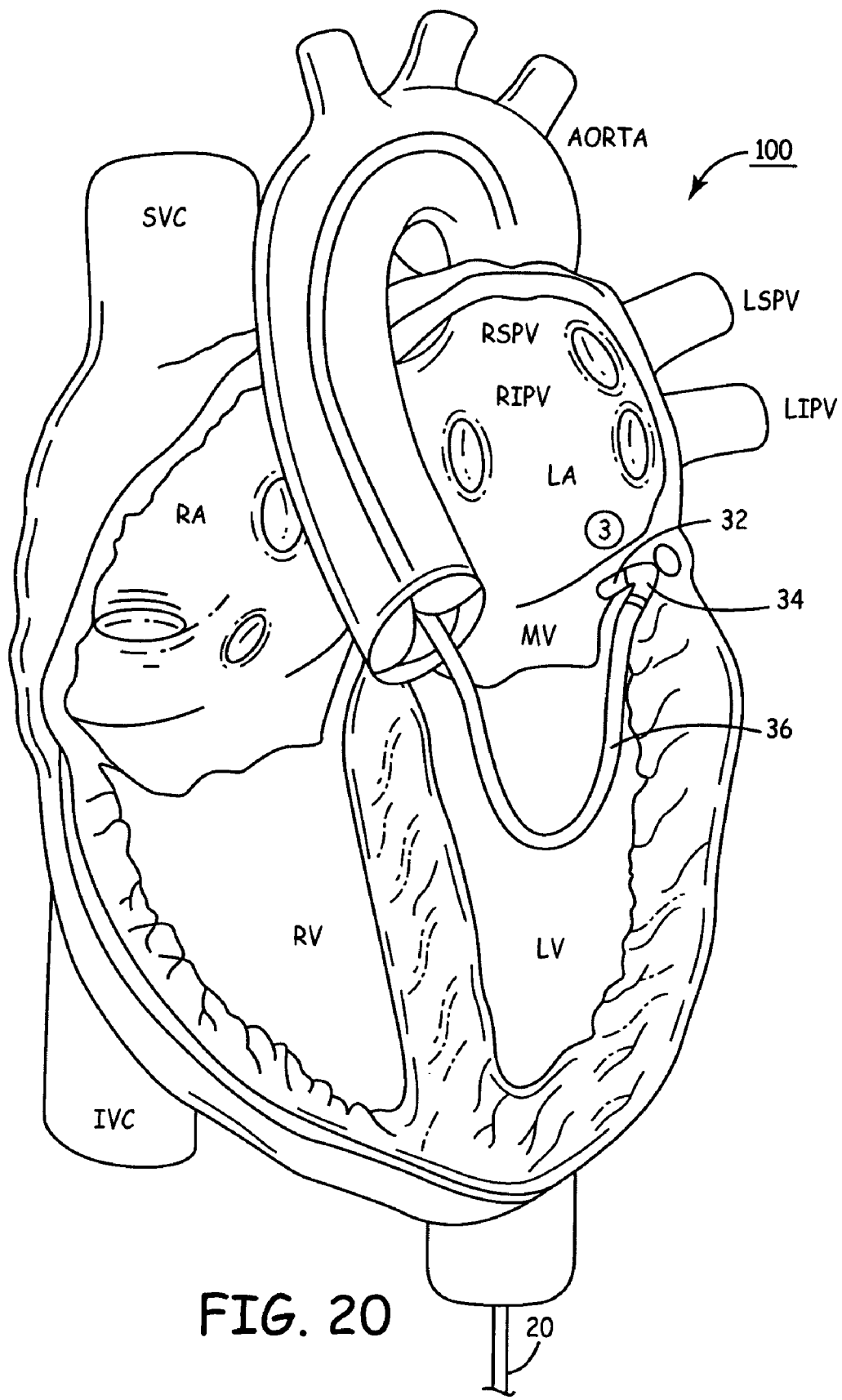

FIGS. 18-20 are schematic illustrations of the selective locations of the distal section 30 of the catheter body 20 of the catheter 10 described above for cardiac mapping and/or ablation of the heart 100. In the following discussion, it will be assumed that the distal tip electrode 12 is first applied to the location of interest, ECG readings are made to determine the existence and location of accessory pathways, and ablation is selectively performed.

FIGS. 18-20 illustrate, in simplified form, a sectioned heart 100 and the major vessels bringing venous blood into the right atrium RA, oxygenated blood into the left atrium LA and the aorta and aortic arch (FIG. 20) receiving oxygenated blood from the left ventricle LV. The venous blood is delivered to the RA through the superior vena cava SVC, the inferior vena cava IVC and the coronary sinus CS which all open into the right atrium RA superior to the annulus of the tricuspid valve leading into the right ventricle. Oxygenated blood from the two lungs is delivered into the left atrium by the left and right, inferior and superior, pulmonary veins LIPV, LSPV, RIPV and RSPV which are superior to the mitral valve. The right and left atria are separated by an inter-atrial septum and the right and left ventricles are separated by a ventricular septum. The tricuspid valve TV and mitral valve MV are not shown completely to simplify the figures.

Accessory pathways develop in several parts of the RA and LA that are reached by the catheter 10 to be mapped and/or ablated in accordance with methods of use thereof of the present invention depicted, for example, in FIGS. 18 and 19, respectively. Certain atrial tachycardias also employ left-sided accessory pathways in tight areas under the cusps of the mitral valve MV that can be reached in the manner depicted in FIG. 20. In these illustrations, it will be understood that the catheter body proximal section is flexible enough so that it curves to traverse the vascular system and is curved within a heart chamber by the heart chamber wall by the catheter body In FIG. 18, the distal section 30 of the catheter body 20 is introduced into the RA through the IVC, and the distal segment 32 is oriented to selected locations of the RA heart wall through selective manipulations of the manipulator rings 42, 44 and 46. The RA is separated into a posterior, smooth walled portion that the SVC, IVC and CS orifices open through and a thin walled trabeculated portion separated by a ridge of muscle which is most prominent superior to the SVC ostium. Vestigial valve flaps can adjoin the IVC and CS orifices in some patient's hearts.

A thickened isthmus or Eustachian ridge extends between the IVC orifice and the medial cusp of the tricuspid valve. Certain atrial flutter tachyarrhythmias are known to be caused by accessory pathways situated in the myocardium at or along the Eustachian ridge toward the annulus of the tricuspid valve, and ablation to create a lesion from the IVC orifice over the Eustachian ridge can be used to sever the accessory pathways therein. In FIG. 18, the distal section of the catheter body is formed into a hook shape within the IVC to "hook" the distal tip electrode over the Eustachian ridge and draw it against the tissue in location 1A. A +150° to +180° knuckle bend is made in the intermediate segment in the manner of FIG. 4 to form this hook shape and access this location 1A.

Alternatively, the distal section is advanced into the RA and a +150° to +180° curve is formed in the proximal segment 36 of the distal section along with the +180° knuckle bend made in the intermediate segment in the combined manner of FIGS. 2 and 4 to access the location 1B. The catheter body 20 is then retracted to apply the distal tip electrode 12 at the distal end of this compound hook shape against the tissue location 1B adjacent or overlying location 1A at the Eustachian ridge.

The heart wall can be mapped and continuous lesions can be made along the Eustachian ridge by successively moving the distal electrode 12 to an adjoining location to location 1A or 1B to sense the heart signals or apply RF ablation energy to the new site. The movement can be effected by twisting the distal segment 32 about the catheter body axis 24 by rotating the lateral deflection manipulator ring and wire and/or by adjusting the curvature in the proximal segment 36.

Other accessory pathways in the inter-atrial septum adjacent the AV node or elsewhere along the RA wall or in the triangle of Koch can be accessed as shown by the exemplary location 1C of the distal tip electrode. In this illustrated example, a +90° knuckle bend is made in the intermediate segment in the manner of FIG. 3, and a further positive direction +90° bend is made in the proximal segment 36. Or, if the entire distal section 30 is within the RA, then the configuration of FIG. 2 can be employed to locate and hold the distal tip electrode against the atrial wall around the AV node at the exemplary location 1C.

Premature activations occur frequently in the LA wall, particularly from pulmonary venous foci around the annular orifices of certain or all of the pulmonary veins RIPV, RSPV, LIPV, LSPV shown in FIG. 19 that cause atrial fibrillation. The LA can be accessed in a retrograde manner through the aorta. However, another convenient approach to the LA is via a puncture made through the inter-atrial septum from the RA employing a transseptal sheath 38 as depicted in FIG. 19. The distal section 30 can be formed with about a +90° knuckle bend is made in the intermediate segment in the manner of FIG. 3 and slight positive, neutral or negative curvatures in the range of about −45° to +45° in the proximal segment 36 as in FIGS. 2, 3, and 4 to align the distal tip to locations 2A, 2B or 2C. Continuous lesions can be made around the selected pulmonary valve orifice by successively moving the distal electrode to the next location and applying RF ablation energy. The movement can be effected by twisting the distal segment about the catheter body axis using the deflection wire and manipulator.

The left-sided accessory pathways for atrial tachycardia in tight areas under the cusps of the mitral valve MV are advantageously accessed by advancing the distal section 30 of catheter body 20 in a retrograde manner through the aorta and into the LV and then angling and advancing the distal tip electrode under the cusps to exemplary location 3 as shown in FIG. 20. The distal segment 32 extends inward in relation to the plane of the drawing of FIG. 20, and can be worked under the cusps around the MV to map and/or ablate a succession of adjoining sites.

While the preferred embodiment only illustrates a single mapping/ablation distal tip electrode 12 particularly used in a unipolar ablation and/or mapping mode, it will be understood that it may be advantageous to locate one or more additional mapping/ablation electrodes in the distal segment 32 and/or proximally in the curvable proximal segment 36 for selective operation either in a unipolar or bipolar mapping/ablation mode. In the latter case, bipolar mapping/ablation across or through the Eustachian ridge can be achieved in the hook configuration depicted in FIG. 4 and at location 1A of FIG. 18.

Figure 24:
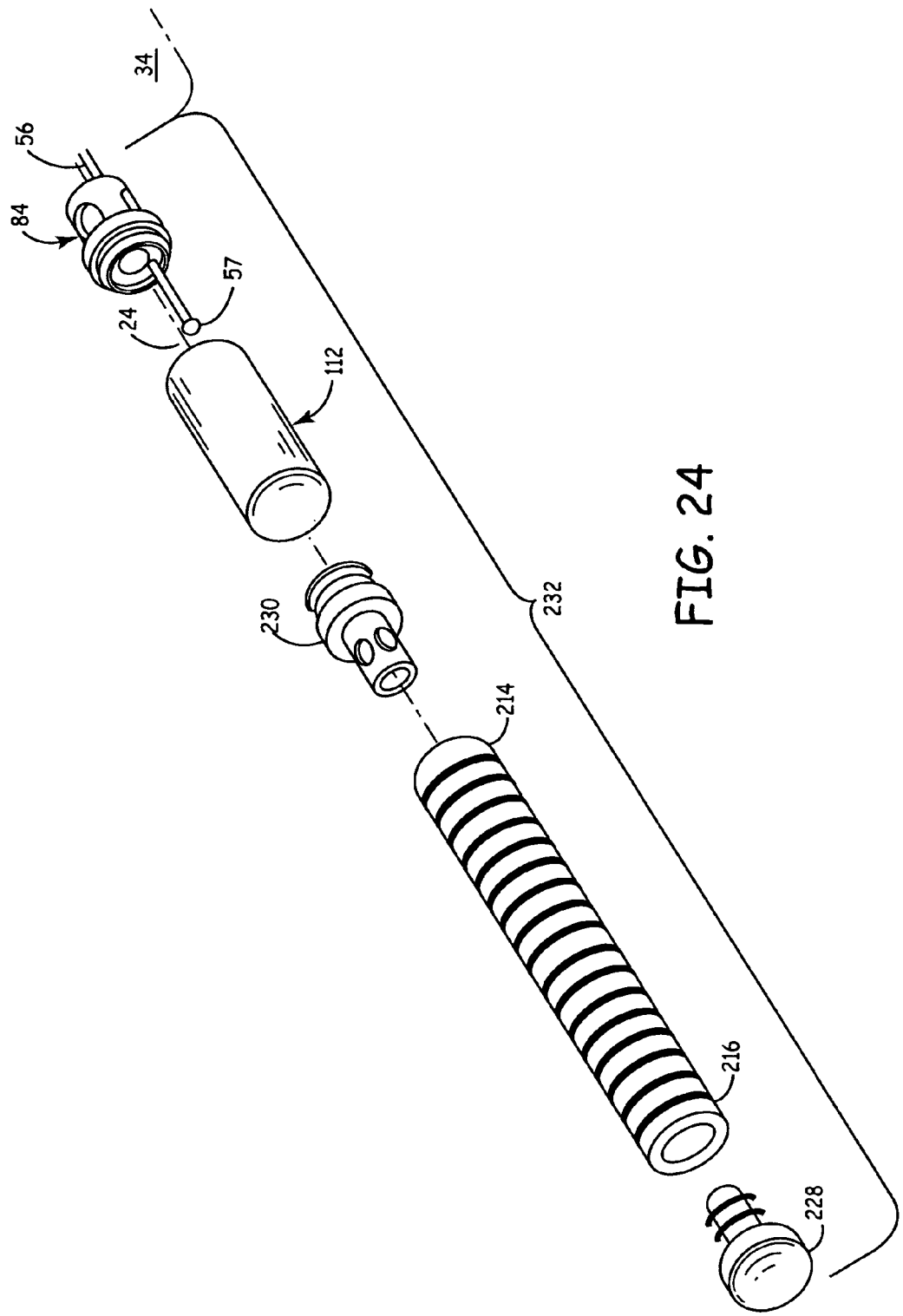
FIG. 24 is a partial perspective exploded view of a still further embodiment of the distal segment of the distal section of the catheter body adapted for use in mapping and ablating the heart wall along the Caval-tricuspid isthmus.
Figure 27:
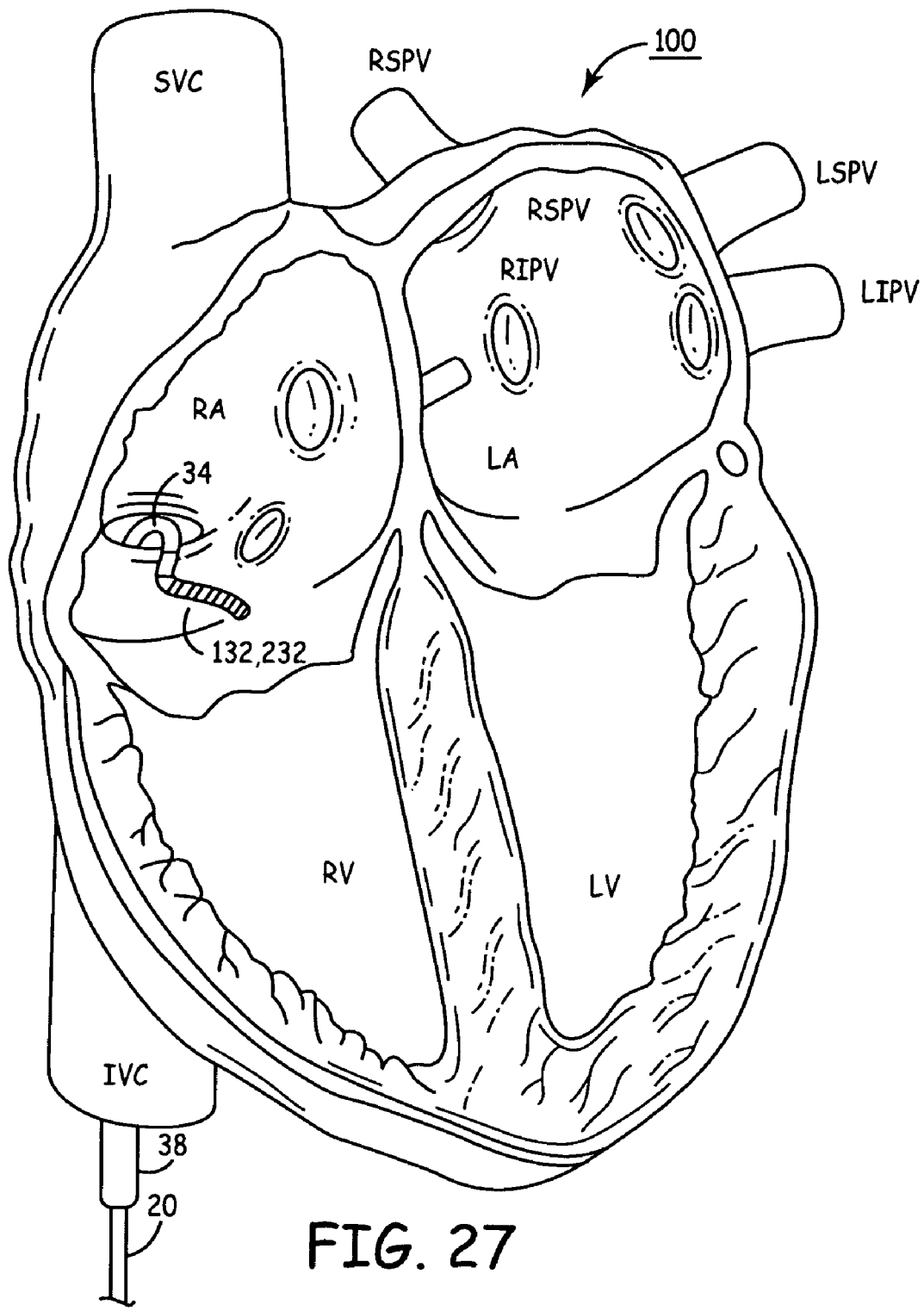
FIG. 27 is a schematic illustration of the location of the distal section of the catheter of FIGS. 21-25 for cardiac mapping and/or ablation along the Caval-tricuspid isthmus.

In further embodiments of the present invention depicted in FIGS. 21-27, particularly for ablating or mapping the Eustachian ridge, a plurality of mapping and/or ablation electrodes are located along extended distal segments 132 and 232 distal to electrode 112 (which can be eliminated in variations to these embodiments). The extended distal segments 132 and 232 are formed to comply to the particular shape of the caval-tricuspid isthmus extending anteriorly from the orifice of the IVC and toward the valve flaps of the tricuspid valve to map and ablate that area as shown in FIG. 27. The extended distal segments 132 and 232 can have a pre-formed curved axis particularly shaped to the surface curvature of the caval-tricuspid isthmus. Or, the extended distal segments 132 and 232 can have an elasticity and flexibility that conforms to the surface curvature of the caval-tricuspid isthmus effected by selection of a suitable low durometer insulating tubular member supporting the electrode(s). In either case, the hook shape is formed in the knuckle bend segment 34 in the manner illustrated in FIGS. 24, 26 and 27, and a positive curve can be induced in the proximal segment 36 as shown in FIGS. 24 or 26 as necessary. A 0° or negative curvature can alternatively be induced in the proximal segment 36 as shown in FIG. 5 if found necessary in a particular heart. From the handle 40 outside the body, it is therefore possible to hook the intermediate segment 34 over the Eustachian ridge to orient the elongated, flexible electrode support body of the distal segments 132, 232 against and in conformance with contours of the heart wall between the Eustachian ridge and the tricuspid valve cusps. A guide sheath or introducer may be required to straighten the pre-formed curvature or the highly flexible distal segment 132, 232 to enable introduction through the vascular system and into the RA.

Figure 21:
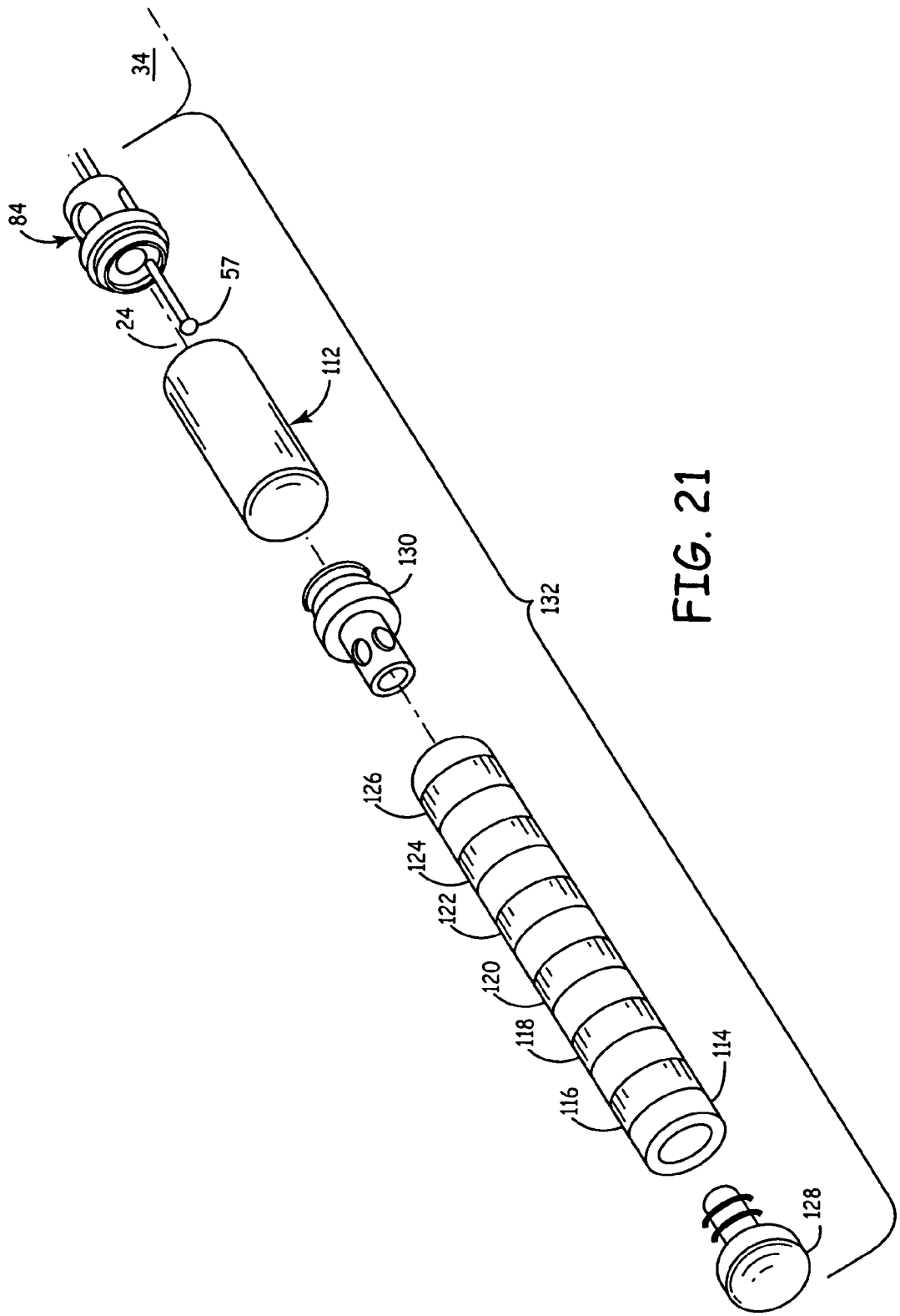
FIG. 21 is a partial perspective exploded view of a further embodiment of the distal segment of the distal section of the catheter body adapted for use in mapping and ablating the heart wall along the Caval-tricuspid isthmus.

The extended distal segment 132 is formed of a plurality (e.g. six) of ring electrodes 116, 118, 120, 122, 124, and 126 supported on a highly flexible or pre-formed electrode support tube 114 as shown in FIGS. 21-23. The proximal end of the extended distal segment 132 including the distal insulator 84 is coupled to the intermediate segment 34 of the catheter otherwise shown in FIGS. 1 and 8-17 and described above. A further insulator 130 separates electrode 112 from the electrode support tube 114, and the distal tip 128 is fitted to the distal end of the electrode support tube 114. The conductors to the electrodes 116, 118, 120, 122, 124, and 126 that traverse the lumens of the electrode support tube 114, the insulator 130, the electrode 112, and the distal insulator 84 are not shown in FIG. 21 to simplify the drawing. Such conductors would be formed of high conductivity metals, e.g., copper, copper-silver alloys, and silver cored wire.

In the alternative embodiment of FIGS. 24-26, the extended distal segment 232 is formed of one or plurality (e.g. two) of spiral wound electrode(s) 216 supported on a highly flexible or pre-formed electrode support tube 214. The proximal end of the extended distal segment 132 including the distal insulator 84 is coupled to the intermediate segment 34 of the catheter otherwise shown in FIGS. 1 and 8-17 and described above. A further insulator 230 separates electrode 112 from the electrode support tube 214, and the distal tip 228 is fitted to the distal end of the electrode support tube 214. The conductor(s) to the electrode(s) 216 that traverse the lumens of the electrode support tube 214, the insulator 230, the electrode 112, and the distal insulator 84 are not shown in FIG. 21 to simplify the drawing. Such conductor(s) would be formed of high conductivity metals, e.g., copper, copper-silver alloys, and silver cored wire.

It is also contemplated that in the embodiments depicted in FIGS. 24-27 may be further modified by eliminating the proximal segment 36 and its associated manipulator structure described above. In such an embodiment, the distal end of the proximal section 22 would be coupled directly to the proximal end of the intermediate segment 34.

In the above-described preferred embodiments, the knuckle bend wire 56 and the curve deflection wire 54 extend through the proximal section 22 and the curvable proximal segment 36, and the knuckle bend wire 56 extends further distally through the bendable intermediate segment 34 in a common radius extending from the catheter body axis 24 as shown in FIGS. 2-16. Therefore, the bend induced in the bendable intermediate segment 34 upon retraction proximally of the knuckle bend wire 56 and the curve induced in the curvable proximal segment 36 upon retraction proximally of the curve deflection wire 54 are in a common plane with respect to the catheter body axis 24 and in a common direction as shown in FIG. 2. The bend induced in the bendable intermediate segment 34 upon retraction proximally of the knuckle bend wire 56 and the curve induced in the curvable proximal segment 36 upon extension distally of the curve deflection wire 54 are in a common plane with respect to the catheter body axis 24 but in a different direction as shown in FIG. 5. The knuckle bend that can be induced in the intermediate segment 34 is very tight, falling within a radius of about 2.0 mm to 7.0 mm through a range of about −90° to about +180° with respect to the catheter body axis 24 at the intermediate segment proximal end.

It will be understood that certain features of the present invention can be advantageously employed in modifications of the preferred embodiment, e.g., by displacing the knuckle bend wire 56 and its associated lumens 68, 83, 93 and 87, in a radius that is not common with the curve deflection wire 54 and its associated lumens. In this regard, the knuckle bend wire 56 and its associated lumens 68, 83, 93 and 87, can be arranged in a radius that is diametrically opposed to the radius that the curve deflection wire 54 and its associated lumens are aligned with, i.e., in a common diametric line but on either side of the catheter body axis 24. The lateral deflection wire 52 and its associate lumens illustrated in the FIGS. 12-16 occupy such a location, and they can be displaced either radially or to the other side of the axis 24. Then, the knuckle bend induced in the intermediate segment 34 would be in the opposite direction than is depicted in FIGS. 2-7.

The catheter shaft or body and handle of the present invention allows manipulation with a high degree of sensitivity and controllability to provide the degree of precision required for proper positioning of the tip electrode(s). The distal section of the catheter body is sufficiently resilient in order to position the distal tip electrode(s) against the endocardium and to maintain the distal tip electrode(s) in position during mapping or ablation without being displaced by movement of the beating heart, by respiration, or by blood flow. Along with steerability, flexibility, and resiliency, the catheter body has a sufficient degree of torsional stiffness to permit user imparted torque to be transmitted to the distal tip electrode(s) from the handle. Moreover, the catheter body has sufficient column strength to convey axial loading to push the distal tip electrode(s) against the tissue at target positions to be mapped or ablated.

Other modification and variation can be made to the disclosed embodiments without departing from the subject of the invention as defined in the following claims. For example, materials, diameters and lengths can be changed to suit the particular needs or desires of the user. A single mapping/ablation electrode, or more than two mapping/ablation electrodes could be present. A plurality of small sized mapping electrodes displaced apart along the distal section of the catheter body are typically provided and paired electrically to increase sensing resolution of the electrical signals of the heart traversing the adjoining heart wall site. Mapping electrodes could also be located between ablation electrodes. In some cases it may be desired to apply energy to more than one ablation electrode at the same time; for example, four ablation electrodes could be used and powered in pairs.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

What is claimed is:

1. A catheter for mapping and/or ablation of heart tissue at a target site of a heart wall comprising:
    a handle;
    a catheter body attached to the handle, the catheter body having a catheter body axis extending through a proximal section and a distal section, the distal section comprising distal, proximal, and intermediate segments and a distal electrode in the distal segment;
    wherein the angular orientation of the distal segment of the catheter body can be altered in relation to the catheter body axis in the proximal section to align the distal electrode with the surface of the heart tissue at the target site;
    means for selectively inducing a knuckle bend in the intermediate segment with respect to the proximal and distal segments independently of a formation of any curving of the proximal segment. the knuckle bend having a radius of between about 2.0 , mm and 7.0 mm through a range of about −90° to about +180° with respect to the catheter body axis; and means for selectively inducing a curve in the proximal segment with respect to the catheter body axis in the proximal section independently of any formation of a knuckle bend in the intermediate segment, the curve having a radius exceeding the radius of the knuckle bend through a range of between about −180° to about +270° with respect to the catheter body axis, whereby the distal electrode is oriented and can be urged from the handle outside the body against the target site with force applied through the catheter body 2. A method for orienting an electrode of a catheter for mapping and/or ablation of heart tissue at a target site of a heart wall comprising the steps of:

providing the catheter for mapping and/or ablation of heart tissue comprising a handle and a catheter body attached at a catheter body proximal end to the handle, the catheter body having a catheter body axis extending through a proximal section and a distal section, the distal section comprising distal, proximal, and intermediate segments and a distal electrode in the distal segment;

passing the distal, proximal, and intermediate segments of the distal section of the catheter body in proximity to heart tissue at the target site of a heart of a patient;

from the handle outside the body, selectively altering the angular orientation of the distal segment in relation to the catheter body axis in the proximal section to align the distal electrode with the surface of the heart tissue at the target site by selectively or collectively:

inducing a knuckle bend in the intermediate segment with respect to the proximal and distal segments independently of a formation of any curving of the proximal segment, the knuckle bend haying a radius of between about 2.0 mm and 7.0 mm through a bending range of between about −90° to about +180° with respect to the catheter body axis; and inducing a curve in the proximal segment with respect to the catheter body axis in the proximal section independently of the any formation of a knuckle bend in the intermediate segment, the curve having a radius exceeding the radius of the knuckle bend through a range of between about −180° to about +270° with respect to the catheter body axis; and from the handle outside the body, urging the distal electrode against the target site with force applied through the catheter body to enable mapping of cardiac signals within and delivery of ablation energy to the adjoining heart wall through said electrode.

* * * * *